(12) United States Patent
Abril

(10) Patent No.: US 8,034,391 B2
(45) Date of Patent: Oct. 11, 2011

(54) POLYUNSATURATED FATTY ACID-CONTAINING OIL PRODUCT AND USES AND PRODUCTION THEREOF

(75) Inventor: Jesus Ruben Abril, Westminster, CO (US)

(73) Assignee: Martek Biosciences Corporation, Columbia, MD (US)

( * ) Notice: Subject to any disclaimer, the term of this patent is extended or adjusted under 35 U.S.C. 154(b) by 1197 days.

(21) Appl. No.: 11/428,277

(22) Filed: Jun. 30, 2006

(65) Prior Publication Data

US 2007/0003686 A1    Jan. 4, 2007

Related U.S. Application Data

(60) Provisional application No. 60/695,996, filed on Jul. 1, 2005, provisional application No. 60/738,304, filed on Nov. 18, 2005.

(51) Int. Cl.
*A23D 9/02* (2006.01)
(52) U.S. Cl. .................. 426/490; 426/417; 426/607
(58) Field of Classification Search .............. 426/417, 426/490
See application file for complete search history.

(56) References Cited

U.S. PATENT DOCUMENTS

| | | | |
|---|---|---|---|
| 4,469,710 A | 9/1984 | Rielley et al. | |
| 4,764,392 A * | 8/1988 | Yasufuku et al. | 426/603 |
| 5,130,242 A | 7/1992 | Barclay | |
| 5,151,291 A * | 9/1992 | Tokairin et al. | 426/581 |
| 5,268,186 A | 12/1993 | Moskowitz | |
| 5,340,594 A | 8/1994 | Barclay | |
| 5,374,445 A | 12/1994 | Havenstein et al. | |
| 5,374,657 A | 12/1994 | Kyle | |
| 5,407,957 A | 4/1995 | Kyle et al. | |
| 5,514,407 A | 5/1996 | Perlman et al. | |
| 5,747,080 A | 5/1998 | Lemke et al. | |
| 5,949,017 A | 9/1999 | Oommen et al. | |
| 5,993,869 A | 11/1999 | Freeport | |
| 6,117,476 A | 9/2000 | Eger et al. | |
| 6,159,525 A * | 12/2000 | Lievense et al. | 426/603 |
| 6,335,370 B1 | 1/2002 | De Mesanstourne et al. | |
| 6,623,782 B2 | 9/2003 | Hori et al. | |
| 7,157,110 B2 | 1/2007 | Loh et al. | |
| 7,435,436 B2 | 10/2008 | Schilmoeller et al. | |
| 2002/0127306 A1 | 9/2002 | Schmidt et al. | |
| 2003/0099747 A1 | 5/2003 | Eini et al. | |
| 2003/0138477 A1 | 7/2003 | Barclay | |
| 2004/0049062 A1 | 3/2004 | Bijl et al. | |
| 2004/0059142 A1 | 3/2004 | Bijl et al. | |
| 2004/0096550 A1 | 5/2004 | Schilmoeller et al. | |
| 2004/0151823 A1 | 8/2004 | Daniels et al. | |
| 2005/0027004 A1 | 2/2005 | Kyle et al. | |
| 2006/0110521 A1 | 5/2006 | Heise et al. | |
| 2007/0003687 A1 | 1/2007 | Abril et al. | |
| 2008/0026103 A1 | 1/2008 | Fichtali et al. | |
| 2008/0107791 A1 | 5/2008 | Fichtali et al. | |
| 2009/0099260 A1 | 4/2009 | Namal Senanayake | |

FOREIGN PATENT DOCUMENTS

| | | |
|---|---|---|
| EP | 0427312 A1 | 5/1991 |
| EP | 0651611 | 5/1995 |
| EP | 0664300 | 7/1995 |
| EP | 0948907 | 10/1999 |
| EP | 1215274 | * 12/2000 |
| EP | 1482814 | 12/2004 |
| EP | 1562448 | 8/2005 |
| GB | 2194876 | 3/1988 |
| JP | 02-203741 | 8/1990 |
| JP | 02-243622 | 9/1990 |
| JP | 3-53846 A | 3/1991 |
| JP | 07-313055 | 12/1995 |
| JP | 8-509355 A | 10/1996 |
| JP | 9-23817 A | 1/1997 |
| JP | 9-75001 A | 3/1997 |
| JP | 9-510364 A | 10/1997 |
| JP | 10-72590 A | 3/1998 |
| WO | WO 91/07498 A1 | 5/1991 |
| WO | WO 93/22933 | 11/1993 |
| WO | WO 95/25433 A1 | 9/1995 |
| WO | WO 97/36996 A2 | 10/1997 |
| WO | WO 97/43362 A1 | 11/1997 |
| WO | WO 00/33668 | 6/2000 |
| WO | WO 00/69273 | 11/2000 |
| WO | WO 03/077675 | 9/2003 |
| WO | WO 03/105606 | 12/2003 |
| WO | WO 2004/045308 | 6/2004 |
| WO | WO 2004/108874 | 12/2004 |
| WO | WO 2004/110168 | 12/2004 |
| WO | WO 2006/004906 | 1/2006 |

OTHER PUBLICATIONS

Huang et al. 2001. JAOCS 78(6)605.* Vali et al. 2003, JAOCX 80(7)725.*
Christie "Chapter 1 The Structure, Chemistry and Occurrence of Lipids", from Lipid Analysis. Isolation, Separation, Identification and Structural Analysis of Lipids, 2nd Edition, 1982, p. 1-16.
Barclay et al., "Microalgae-based ingredients are useful vegetarian sources of DHA n-3 for functional foods", May 16, 2001, 6 pages.
Stagnitti et al., "Fermented fortification", Dairy Industries International, Jun. 2001, p. 26-27.
Stagnitti "Functional confectionery—sweetening the omega-3 'pill'", date unknown, p. 60.

(Continued)

*Primary Examiner* — Carolyn Paden
(74) *Attorney, Agent, or Firm* — Sterne, Kessler, Goldstein & Fox P.L.L.C.

(57) ABSTRACT

The present invention includes a solid fat composition that includes an oil having saturated fat and a microbial oil having a long chain polyunsaturated fatty acid and an emulsifier. In particular, the solid fat composition can have high levels of long chain polyunsaturated fatty acid and low amounts of emulsifiers. In preferred embodiments, the polyunsaturated oil is an unwinterized microbial oil. The invention also relates to methods for making such compositions and food, nutritional, and pharmaceutical products comprising said compositions. The present invention also includes a microbial oil product prepared by extracting an oil-containing fraction comprising at least one LC-PUFA from a microbial biomass, and treating the fraction by a process of vacuum evaporation, wherein the oil product has not been subject to one or more of a solvent winterization step, a caustic refining process, a chill filtration process, or a bleaching process.

30 Claims, 3 Drawing Sheets

OTHER PUBLICATIONS

International Preliminary Report on Patentablity for International (PCT) Patent Application No. PCT/US06/25797, mailed Jan. 17, 2008.

Kuntz, "Designer Fats for Bakery," *Food Product Design* Nov. 2002.

Fischer, "Sorting Fat from Fiction," *Prepared Foods* Dec. 10, 2003, available at http://www.preparedfoods.com/CDA/Archives/938d322e33788010VgnVCM100000f932a8c0.

International Search Report for International (PCT) Patent Application No. PCT/US06/25797, mailed Oct. 11, 2007.

Written Opinion for International (PCT) Patent Application No. PCT/US06/25797, mailed Oct. 11, 2007.

English language Abstract of Japanese Patent Publication No. JP 3-53846 A, European Patent Office, Espacenet database, Worldwide (1991).

English language Abstract of Japanese Patent Publication No. JP 9-23817 A, European Patent Office, Espacenet database, Worldwide (1997).

English language Abstract of Japanese Patent Publication No. JP 9-75001 A, European Patent Office, Espacenet database, Worldwide (1997).

English language Abstract of Japanese Patent Publication No. JP 10-72590 A, European Patent Office, Espacenet database, Worldwide (1998).

"Sensory Evaluation of Microwavable Popcorn", Columbia Site Sensory Evaluations, 1 page, Martek Biosciences Corporation, (Feb. 2006).

Certik, M. and Shimizu, S., " Biosynthesis and regulation of microbial polyunsaturated fatty acid production," *J. Biosci. Bioeng.* 87(1):1-14, Society for Bioscience and Bioengineering, Japan (1999).

Frankel, Edwin N., "Chapter 10: Food," in *Lipid Oxidation*, The Oily Press Ltd., UK, pp. 187-225, (1998).

Innis, S.M. and Hansen, J.W., " Plasma fatty acid responses, metabolic effects, and safety of microalgal and fungal oils rich in arachidonic and docosahexaenoic acids in healthy adults," *Am. J. Clin. Nutr.* 64(2):159-67, American Society of Clinical Nutrition, United States (1996).

Jadhav, S.J., et al., "Lipid Oxidation in Biological and Food Systems," in *Food Antioxidants*, Madhavi et al., eds, Marcel Dekker, New York, pp. 5-63, (1996).

Labuza, T.P., et al., "Kinetics of Lipid Oxidation," *CRC Critical Reviews in Food Technology* 2(3):355-405, (1971).

Ward, O.P. and Singh, A., "Omega-3/6 fatty acids: Alternative sources of production," *Process Biochemistry* 40(12):3627-3652, Elsevier Applied Science, England (2005).

Warner, K., "7. Chemistry of Frying Oils," in *Food Lipids: Chemistry, Nutrition, and Biotechnology*, 3rd Edition, Akoh, et al., eds., CRC Press, USA, pp. 205-222, (1998).

"Know Your Fats," American Heart Association Learn and Live, content last updated Jan. 29, 2010, accessed at <http://www.americanheart.org/presenter.jhtml?identifier=532>, on Mar. 24, 2010.

International Search Report for International (PCT) Patent Application No. PCT/US08/74790, ISA/US, Commissioner for Patents, United States, mailed Nov. 28, 2008.

International Search Report and Written Opinion for International (PCT) Application No. PCT/US06/25799, ISA/US, Commissioner for Patents, United States, mailed Jun. 3, 2008.

Office Action mailed Aug. 19, 2010, in U.S. Appl. No. 11/748,330, Fichtali et al., filed May 14, 2007.

Office Action mailed May 13, 2010, in U.S. Appl. No. 11/470,996, Fichtali et al., filed Sep. 7, 2006.

Office Action mailed May 20, 2010, in U.S. Appl. No. 11/428,296, Fichtali et al., filed Jun. 30, 2006.

Office Action mailed Sep. 24, 2009, in U.S. Appl. No. 11/428,296, Fichtali et al., filed Jun. 30, 2006.

\* cited by examiner

MINIMALLY PROCESSED PUFA OILS

POLYUNSATURATED FATTY ACID-CONTAINING OIL PRODUCT AND USES AND PRODUCTION THEREOF

CROSS REFERENCE TO RELATED APPLICATIONS

This application claims priority under 35 U.S.C. § 119(e) to U.S. Provisional Patent Application Ser. No. 60/695,996 filed Jul. 1, 2005, and to U.S. Provisional Patent Application Ser. No. 60/738,304, filed Nov. 18, 2005, each of which is incorporated herein in its entirety by this reference.

FIELD OF THE INVENTION

The invention relates to a polyunsaturated fatty acid-containing oil product and uses thereof, such as in a solid fat composition that includes a microbially-derived long chain polyunsaturated fatty acid and a thickener. The invention also relates to methods for making such products and food, nutritional, and pharmaceutical products comprising said compositions.

BACKGROUND OF THE INVENTION

It is desirable to increase the dietary intake of many beneficial nutrients. Particularly beneficial nutrients include fatty acids such as omega-3 and omega-6 long chain polyunsaturated fatty acids (LC-PUFA). Omega-3 PU-PUFAs are recognized as important dietary compounds for preventing arteriosclerosis and coronary heart disease, for alleviating inflammatory conditions and for retarding the growth of tumor cells. Omega-6 PUFAs serve not only as structural lipids in the human body, but also as precursors for a number of factors in inflammation such as prostaglandins, and leukotrienes. An important class of both the omega-3 and the omega-6 PUFAs is long chain omega-3 and the omega-6 PUFAs.

Fatty acids are classified based on the length and saturation characteristics of the carbon chain. Short chain fatty acids have 2 to about 6 carbons and are typically saturated. Medium chain fatty acids have from about 6 to about 14 carbons and are also typically saturated. Long chain fatty acids have from 16 to 24 or more carbons and may be saturated or unsaturated. In longer chain fatty acids there may be one or more points of unsaturation, giving rise to the terms "monounsaturated" and "polyunsaturated," respectively. Long chain PUFAs (LC-PUFAs) having 20 or more carbons are of particular interest in the present invention.

LC-PUFAs are categorized according to the number and position of double bonds in the fatty acids according to a well understood nomenclature. There are two main series or families of LC-PUFAs, depending on the position of the double bond closest to the methyl end of the fatty acid: the omega-3 series contains a double bond at the third carbon, while the omega-6 series has no double bond until the sixth carbon. Thus, docosahexaenoic acid ("DHA") has a chain length of 22 carbons with 6 double bonds beginning with the third carbon from the methyl end and is designated "22:6 n-3". Other important omega-3 LC-PUFAs include eicosapentaenoic acid ("EPA") which is designated "20:5 n-3," andomega-3 docosapentaenoic acid ("DPA") which is designated "22:5 n-3." Important omega-6 LC-PUFAs include arachidonic acid ("ARA") which is designated "20:4 n-6," and omega-6 docosapentaenoic acid ("DPA") which is designated "22:5 n-6."

De novo or "new" synthesis of the omega-3 and omega-6 essential fatty acids does not occur in the human; however, the body can convert these essential fatty acids, when obtained in the diet, to LC-PUFAs such as DHA and ARA although at very low efficiency. Both omega-3 and omega-6 fatty acids must be part of the nutritional intake since the human body cannot insert double bonds closer to the omega end than the seventh carbon atom counting from that end of the molecule. Thus, all metabolic conversions occur without altering the omega end of the molecule that contains the omega-3 and omega-6 double bonds. Consequently, omega-3 and omega-6 acids are two separate families of fatty acids since they are not interconvertible in the human body.

Over the past twenty years, health experts have recommended diets lower in saturated fats and higher in polyunsaturated fats. While this advice has been followed by a number of consumers, the incidence of heart disease, cancer, diabetes and many other debilitating diseases has continued to increase steadily. Scientists agree that the type and source of polyunsaturated fats is as critical as the total quantity of fats. The most common polyunsaturated fats are derived from vegetable matter and are lacking in long chain fatty acids (most particularly omega-3 LC-PUFAs). In addition, the hydrogenation of polyunsaturated fats to create synthetic fats has contributed to the rise of certain health disorders and exacerbated the deficiency in some essential fatty acids. Indeed, many medical conditions have been identified as benefiting from omega-3 supplementation. These include acne, allergies, Alzheimer's, arthritis, atherosclerosis, breast cysts, cancer, cystic fibrosis, diabetes, eczema, hypertension, hyperactivity, intestinal disorders, kidney dysfunction, leukemia, and multiple sclerosis. Of note, the World Health Organization has recommended that infant formulas be enriched with omega-3 fatty acids.

The conventionally used polyunsaturates are those derived from vegetable oils, which contain significant amounts of omega-6 (C18:2 n-6) but little or no omega-3. While omega-6 and omega-3 fatty acids are both necessary for good health, it is recommended that they be consumed in a balance of about 4:1. Principal sources of omega-3 are flaxseed oil and fish oils. The past decade has seen rapid growth in the production of flaxseed and fish oils. Both types of oil are considered good dietary sources of omega-3 polyunsaturated fats. Flaxseed oil contains no EPA, DHA, DPA or ARA but rather contains linolenic acid (C18:3 n-3), a building block enabling the body to manufacture EPA. There is evidence however that the rate of metabolic conversion can be slow and unsteady, particularly among those with impaired health. Fish oils vary considerably in the type and level of fatty acid composition depending on the particular species and their diets. For example, fish raised by aquaculture tend to have a lower level of omega-3 fatty acids than those in the wild. Furthermore, fish oils carry the risk of containing environmental contaminants commonly found in fish. In light of the health benefits of such omega-3 and omega-6 LC-PUFAs (chain length greater than 20), it would be desirable to supplement foods with such fatty acids.

Liquid oils such as fish oils and certain microbial oils are known to contain a high content of LC-PUFAs. However, due to their polyunsaturated nature, these oils are not solid at room temperature (i.e., 20° C.), rather being in an oil, or liquid, form. However, solid forms of PUFA-rich oils are desirable for use in certain food applications where liquid oils are not applicable. To form a solid composition, a number of approaches have been tried. A common process used to solidify unsaturated oils consists of partial or full hydrogenation of such oils, so as to obtain semi-solid oils. Yet, as a result of this chemical transformation, the oils become saturated and lose their healthy properties. The partial hydrogenation process also results in the formation of "trans"-fatty acids, which have been shown to possess several adverse properties. Hence, by solidifying unsaturated oils using a hydrogenation process, the beneficial properties of the unsaturated oils are substituted by the highly undesirable adverse properties of the saturated oils and the formation of "trans"-fatty acids. Other methods include mixing the unsaturated oils with "hard" or saturated fats so that the mixture is a semi-solid oil. Again, the benefits of the "healthy" unsaturated oil are at least partially offset by the presence of hardened, or saturated, fats. Other methods for forming a spreadable, semi-solid fat composition comprising high levels of polyunsaturated fats include using high levels of particular types of emulsifiers, or other thickeners such as fatty alcohols. Until the present invention, there was lacking in the art compositions comprising a solid or semi-solid fat or food product containing high levels of PUFAs, but without exogenously added saturated fats, high levels of exogenously-added emulsifiers and/or other types of thickeners. Such compositions and methods to form such compositions would be highly desirable. It would be further desirable to provide a low cost method for making such a composition, said method involving the use of non-hazardous materials, minimal processing steps, and minimal raw material inventory.

Liquid oils such as, microbial oils, known to contain a high content of LC-PUFAs are typically processed for consumption by humans or other animals by multiple steps, including pretreatment, desolventization or deodorization, winterization, caustic refining (also known as chemical refining), chill filtration, and bleaching. Such processes add time and cost to preparation of products and can introduce chemicals in the refining process unacceptable for the natural or organic products market. Accordingly, there is a need for improved methods of producing oils that are simplified, less costly and acceptable to broad markets, while still being effective for producing products having acceptable organoleptic properties.

SUMMARY OF THE INVENTION

The present invention provides a method for producing a solid fat composition comprising mixing an oil comprising saturated fat and a microbial oil comprising at least one LC-PUFA with at least one emulsifier to form a mixture; and solidifying the mixture to form a solid fat composition. The invention also provides a solid fat composition comprising a mixture of an unwinterized microbial oil comprising an LC-PUFA and an emulsifier, wherein the mixture is a solid composition at room temperature.

In some embodiments of the method, the oil comprises between about 5 wt. % and about 70 wt. % LC-PUFA and between about 20 wt. % and about 60 wt. % saturated fat.

In some embodiments, the solid fat composition comprises saturated fat.

In some embodiments, the saturated fat is not added exogenously, and in other embodiments, the saturated fat is added exogenously. In further embodiments, the microbial oil is unwinterized or not hydrogenated.

In some embodiments, the microbial oil is from a microorganism selected from the group consisting of microorganisms of the genus *Thraustochytrium*, microorganisms of the genus *Schizochytrium*, microorganisms of the genus *Althornia*, microorganisms of the genus *Aplanochytrium*, microorganisms of the genus *Japonochytrium*, microorganisms of the genus *Labyrinthula*, microorganisms of the genus *Labyrinthuloides*, microorganisms of the genus *Crypthecodinium*, and mixtures thereof. In further embodiments, the microorganism is selected from the group consisting of microorganisms of the genus *Thraustochytrium*, microorganisms of the genus *Schizochytrium*, microorganisms of the genus *Crypthecodinium*, and mixtures thereof.

In some embodiments, the microbial oil comprises an LC-PUFA having a carbon chain length of at least 20, or at least 22, or has at least three double bonds, or has at least four double bonds. In some embodiments, the LC-PUFA comprises docosahexaenoic acid, or docosapentaenoic acid, or arachidonic acid, or eicosapentaenoic acid. In other embodiments, the oil comprises at least about 50 weight percent docosahexaenoic acid, or at least about 60 weight percent docosahexaenoic acid.

In some embodiments, the solid fat composition has a homogeneous texture, or is a shortening.

In some embodiments, the emulsifier is a monoglyceride, a diglyceride, a mono/diglyceride combination, a lecithin, a lactylated mono-di glyceride, a polyglycerol ester, a sucrose fatty acid ester, a sodium steroyl lactylate, a calcium steroyl lactylate, or combinations thereof. In further embodiments, the emulsifier is present in an amount of between about 0.01 weight percent and about 2.0 weight percent, and in further embodiments, between about 0.05 weight percent about 0.2 weight percent.

In some embodiments of the method, the solid fat composition has a melting temperature of at least about 20° C., at least about 30° C., or at least about 35° C.

In some embodiments of the method, the step of solidifying the mixture controls formation of crystals in the solid fat composition. In embodiments of the solid fat composition, the composition comprises crystals, and in some embodiments, the crystals comprise U-prime crystals. In further embodiments of the method or the solid fat composition, the crystals comprise β-prime crystals, at least about 50 wt. % of the fats and/or oils in the solid fat composition are in the β-prime crystal form, or at least about 80 wt. % of the fats and/or oils in the solid fat composition are in the β-prime crystal form.

In some embodiments of the method, the oil and/or emulisifer is heated, heated prior to the mixing step, or heated to at least about 40° C.

In some embodiments of the method, the mixing step comprises agitating the mixture, and in further embodiments, the step of agitating forms a continuous mixture.

In some embodiments of the method, the step of solidifying the mixture comprises cooling the mixture, and in further embodiments, the step of cooling comprises cooling the mixture to a temperature of about 0° C. to about 3° C., or the step of solidifying further comprises mixing the mixture during the step of cooling, or the mixture is cooled at a rate of between about 1° C./min and about 20° C./min.

In some embodiments of the method, the step of solidifying comprises introducing nitrogen into the mixture, and can comprise bubbling nitrogen through the mixture.

The method can further comprise adding at least one additional ingredient to the mixture, including a water-soluble liquid, including water. The water-soluble liquid can be added at an amount between about 1 wt. % and about 10 wt. %.

The composition can further comprise at least one additional ingredient, including a water-soluble liquid, including water. The water-soluble liquid can be present in an amount between about 1 wt. % and about 10 wt. %.

The additional ingredient can also be antioxidants, flavors, flavor enhancers, sweeteners, pigments, vitamins, minerals, pre-biotic compounds, pro-biotic compounds, therapeutic ingredients, medicinal ingredients, functional food ingredients, processing ingredients, or combinations thereof.

In some embodiments, the additional ingredient is ascorbic acid or a salt of ascorbic acid, and in some embodiments is added in an amount between about 0.5 wt. % and about 5 wt. %.

In some embodiments, the additional ingredient is an antioxidant, and in some embodiments is ascorbyl palmitate, tocopherols, citric acid, ascorbic acid, tertiary butyl hydroquinone, rosemary extract, lecithin, or mixtures thereof.

In some embodiments, the solid fat composition has an OSI value of at least about 20, at least about 40, or at least about 60.

In some embodiments of the method, the solid fat composition is selected from the group consisting of a food product, a nutritional product and a pharmaceutical product.

In some embodiments of the method, the method further comprises adding the solid fat composition to a product selected from the group consisting of a food product, a nutritional product and a pharmaceutical product.

The present invention also provides a fat composition comprising an unwinterized microbial oil comprising between about 5 wt. % and about 70 wt. % LC-PUFA and between about 20 wt. % and about 60 wt. % saturated fat; and between about 0.01 wt. % and about 2.0 wt. % of an emulsifier, wherein the composition comprises less than about 10 wt. % of water and wherein the composition is a solid composition at room temperature.

In an additional embodiment, the invention provides a method of preparing an oil product that is used for consumption, comprising extracting an oil-containing fraction from a microbial biomass, wherein the oil-containing fraction comprises at least one LC-PUFA and saturated fatty acids at least sufficient to visually affect the oil-containing fraction; and treating the oil-containing fraction by vacuum evaporation to produce an oil product comprising at least one LC-PUFA, wherein the oil product has not been subject to a winterization step. The present invention also provides an oil product produced by the method.

The invention also provides a microbial oil product that is used for consumption prepared by extracting an oil-containing fraction from a microbial biomass, wherein the oil-containing fraction comprises at least one LC-PUFA and saturated fatty acids at least sufficient to visually affect the oil-containing fraction, and treating the fraction by a process of vacuum evaporation, wherein the oil product is not subjected to a winterization step.

In some embodiments of the method, the oil product has not been subject to a caustic refining process. In other embodiments, the oil product has not been subject to a chill filtration process, and in other embodiments, the oil product has not been subject to a bleaching process.

In some embodiments of the method, the oil-containing fraction can comprise an LC-PUFA having a carbon chain length of at least 20, at least 22, having at least three double bonds, or at least four double bonds. In some embodiments, the LC-PUFA can comprise docosahexaenoic acid, docosapentaenoic acid, arachidonic acid, or eicosapentaenoic acid.

In some embodiments of the method, the step of treating the oil-containing fraction comprises desolventization. In further embodiments, the desolventization can comprise subjecting the extracted oil-containing fraction to vacuum conditions at high temperature, including, but not limited to temperatures from about 50° C. to about 70° C. The desolventization can also comprise subjecting the extracted oil-containing fraction to a vacuum of greater than a vacuum of about 100 mm Hg, subjecting the extracted oil-containing fraction to a vacuum of greater than a vacuum of about 70 mm Hg, or subjecting the extracted oil-containing fraction to a vacuum of greater than a vacuum of about 50 mm Hg.

In some embodiments of the method, the step of treating the oil-containing fraction comprises deodorization. In further embodiments, the deodorization comprises subjecting the extracted oil-containing fraction to vacuum conditions at high temperature while sparging the extracted oil-containing fraction with steam. In one aspect, the high temperature is from about 190° C. to about 220° C. In this embodiment, the desolventization can comprise subjecting the extracted oil-containing fraction to a vacuum of greater than a vacuum of about 25 mm Hg, subjecting the extracted oil-containing fraction to a vacuum of greater than a vacuum of about 12 mm Hg, or subjecting the extracted oil-containing fraction to a vacuum of greater than a vacuum of about 6 mm Hg.

In some embodiments of the method, the oil product has been subjected to the step of bleaching either before or after the step of treating. In other embodiments, the method further comprises fractionating the oil into an olein fraction and a stearin fraction. In other embodiments, the oil product is used for human consumption.

In some embodiments, the oil product has not been subject to a caustic refining process, a chill filtration process, or a bleaching process.

In some embodiments, the microbial biomass is from a microorganism selected from the group consisting of microorganisms of the genus *Thraustochytrium*, microorganisms of the genus *Schizochytrium*, microorganisms of the genus *Althornia*, microorganisms of the genus *Aplanochytrium*, microorganisms of the genus *Japonochytrium*, microorganisms of the genus *Labyrinthula*, microorganisms of the genus *Labyrinthuloides*, microorganisms of the genus *Crypthecodinium*, and mixtures thereof. In other embodiments, the microbial biomass is from a microorganism selected from the group consisting of microorganisms of the genus *Schizochytrium*, microorganisms of the genus *Crypthecodinium*, and mixtures thereof.

In some embodiments, the oil product has a free fatty acid content of less than about 0.5 wt. %, and in other embodiments, has a free fatty acid content of less than about 0.3 wt. %.

In some embodiments, the oil product has a phosphorous value of less than about 10 ppm, and in other embodiments, has a phosphorous value of less than about 5 ppm.

In some embodiments, the oil product has a peroxide value of less than about 2 meq/kg, and in other embodiments, a peroxide value of less than about 1 meq/kg.

In some embodiments, the oil product has an anisidine value of less than about 5, and in other embodiments, has an anisidine value of less than about 3.

In some embodiments, the oil product has a soap content of less than about 5 wt. %, and in other embodiments, has a soap content of less than about 2.5 wt. %.

In some embodiments, the oil product has an Fe concentration of less than about 1 ppm, and in other embodiments, has an Fe concentration of about 0.5 ppm.

In some embodiments, the oil product has a Pb concentration of less than about 1 ppm, and in other embodiments, has a Pb concentration of about 0.2 ppm.

In some embodiments, the oil product has an Hg concentration of less than about 0.1 ppm, and in other embodiments, has an Hg concentration of about 0.04 ppm.

In some embodiments, the oil product has an Ni concentration of less than about 0.1 ppm, and in other embodiments, the oil product has an Ni concentration of about 0.01 ppm.

In some embodiments, the oil product has a Cu concentration of less than about 1 ppm, and in other embodiments, has a Cu concentration of about 0.2 ppm.

The present invention also provides a nutritional product comprising the microbial oil product, a pharmaceutical product comprising the microbial oil product, and a food product comprising the microbial oil product and a food or liquid component. In some embodiments, the pharmaceutical product further comprises a pharmaceutically acceptable excipient. In other embodiments, the pharmaceutical product further comprises a pharmaceutically active agent selected from the group consisting of statins, anti-hypertensive agents, anti-diabetic agents, anti-dementia agents, anti-depressants, anti-obesity agents, appetite suppressants and agents to enhance memory and/or cognitive function.

In some embodiments, the food product is selected from the group consisting of doughs, batters, baked food, liquid food products, semi-solid food products, food bars, processed meats, ice creams, frozen desserts, frozen yogurts, waffle mixes, salad dressings, replacement egg mixes, salted snacks, specialty snacks, dried fruit snacks, meat snacks, pork rinds, health food bars, rice/corn cakes, and confectionary snacks.

In some embodiments, the microbial oil product is used for human consumption.

The present invention also provides a microbial oil product that is used for consumption prepared by a process, comprising extracting an oil-containing fraction comprising at least one LC-PUFA from a microbial biomass; and treating the fraction by a process of vacuum evaporation, wherein the oil product is not subjected to a winterization step, a caustic refining process, a chill filtration process, or a bleaching process; and wherein the oil product has a characteristic selected from the group consisting of a free fatty acid content of less than about 0.5 wt. %, a phosphorous value of less than about 10 ppm, a peroxide value of less than about 2 meq/kg, an anisidine value of less than about 5, a soap content of less than about 5 wt. %, an Fe concentration of less than about 1 ppm, a Pb concentration of less than about 1 ppm, an Hg concentration of less than about 0.1 ppm, an Ni concentration of less than about 0.1 ppm, and a Cu concentration of less than about 1 ppm.

Also provided is a food product comprising the microbial oil product and a food or liquid component, a nutritional product comprising the microbial oil product, and a pharmaceutical product comprising the microbial oil product.

In some embodiments, the microbial oil product is used for human consumption.

The invention also provides a method of preparing an oil product that is used for consumption, comprising extracting an oil-containing fraction from a microbial biomass, wherein the oil-containing fraction comprises at least one LC-PUFA; and treating the oil-containing fraction by vacuum evaporation to produce an oil product comprising at least one LC-PUFA, wherein the oil product has not been subject to a caustic refining process. The present invention also provides an oil product produced by this method.

In some embodiments, the microorganism is a microorganism of the genus *Mortierella*.

In some embodiments, the oil-containing fraction comprises arachidonic acid.

The invention also provides a blended oil product, comprising: an oil product produced a method comprising extracting an oil-containing fraction from a microbial biomass, wherein the oil-containing fraction comprises at least one LC-PUFA and saturated fatty acids at least sufficient to visually affect the oil-containing fraction; and treating the oil-containing fraction by vacuum evaporation to produce an oil product comprising at least one LC-PUFA, wherein the oil product has not been subject to a winterization step; and an oil product produced by a method of comprising extracting an oil-containing fraction from a microbial biomass, wherein the oil-containing fraction comprises at least one LC-PUFA, and treating the oil-containing fraction by vacuum evaporation to produce an oil product comprising at least one LC-PUFA, wherein the oil product has not been subject to a caustic refining process.

In some embodiments, the microbial biomass from which the former oil product was produced is from a microorganism selected from the group consisting of microorganisms of the genus *Thraustochytrium*, microorganisms of the genus *Schizochytrium*, microorganisms of the genus *Althornia*, microorganisms of the genus *Aplanochytrium*, microorganisms of the genus *Jajonochytrium*, microorganisms of the genus *Labyrinthula*, microorganisms of the genus *Labyrinthuloides*, microorganisms of the genus *Crypthecodinium*, and mixtures thereof. In further embodiment, the microorganism is selected from the group consisting of microorganisms of the genus *Schizochytrium*, microorganisms of the genus *Crypthecodinium*, and mixtures thereof.

In a further embodiment of the blended oil product, the microbial biomass from which the latter oil product was produced is from a microorganism of the genus Mortierella.

In a further embodiment, the blended oil product comprises docosahexaenoic acid and arachidonic acid.

In any of the embodiments of the present invention, in one aspect, an oil product produced by a process or method of the invention is a solid at 20° C.

DETAILED DESCRIPTION OF THE INVENTION

Figure 1:
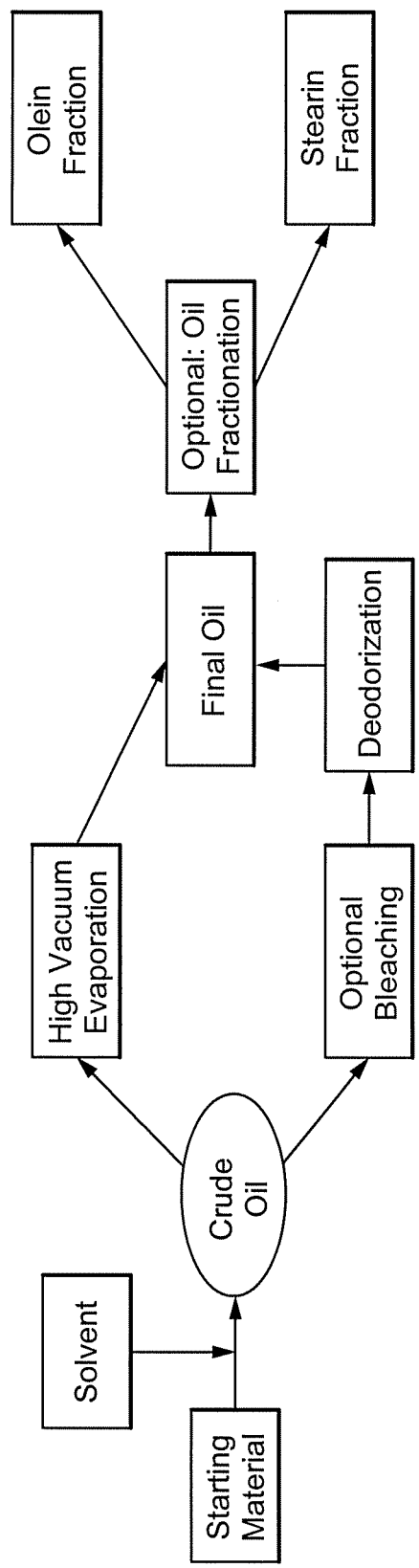
FIG. 1 illustrates various alternative embodiments of the present invention for producing a PUFA-containing oil of the present invention.

The food, nutritional, and pharmaceutical product compositions and methods for preparation of the same, as taught by the present invention, allow for increased intake of nutrients, particularly LC-PUFAs, particularly omega-3 and omega-6 LC-PUFAs, which can provide health benefits to those consuming such products. The present invention is directed in part towards a high-quality PUFA-containing oil product prepared with minimal processing that has improved functionality, improved stability and is compatible with a broad range of applications including the natural and/or organic market sector. One particularly preferred use of such oil products is in the production of a solid fat composition comprising LC-PUFAs that can be used in, or as a, nutritional product, a food product, and/or a pharmaceutical product (medicinal and/or therapeutic). The oils for making products of the invention are microbial oils containing LC-PUFAs derived from a microbial biomass.

A first embodiment of the present invention is a process for producing minimally processed microbial oils that are high-quality PUFA-containing oil products. The process includes extracting an oil-containing fraction comprising at least one LC-PUFA from a microbial biomass to produce a microbial oil. Microbial sources and methods for growing microorganisms comprising nutrients and/or LC-PUFAs for recovery in microbial oils are known in the art (*Industrial Microbiology and Biotechnology*, 2$^{nd}$ edition, 1999, American Society for Microbiology). Preferably, the microorganisms are cultured in a fermentation medium in a fermentor. The methods and compositions of the present invention are applicable to any industrial microorganism that produces LC-PUFA.

Microbial sources can include a microorganism such as an algae, bacteria, fungi (including yeast) and/or protist. Preferred organisms include those selected from the group consisting of golden algae (such as microorganisms of the kingdom Stramenopiles), green algae, diatoms, dinoflagellates (such as microorganisms of the order Dinophyceae including members of the genus *Crypthecodinium* such as, for example, *Crypthecodinium cohnii*), yeast, and fungi of the genera *Mucor* and *Mortierella*, including but not limited to *Mortierella alpina* and *Mortierella* sect. *schmuckeri*. Members of the microbial group Stramenopiles include microalgae and algae-like microorganisms, including the following groups of microorganisms: Hamatores, Proteromonads, Opalines, Develpayella, Diplophrys, Labrinthulids, Thraustochytrids, Biosecids, Oomycetes, Hypochytridiomycetes, Commation, Reticulosphaera, Pelagomonas, Pelagococcus, Ollicola, Aureococcus, Parmales, Diatomns, Xanthophytes, Phaeophytes (brown algae), Eustigmatophytes, Raphidophytes, Synurids, Axodines (including Rhizoctiromulinaales, Pedinellales, Dictyochales), Clrysomeridales, Sarcinochiysidales, Hydrurales, Hibberdiales, and Cluomulinales. The Thraustochytrids include the genera *Schizochytrium* (species include *aggregatum, limnaceum, mangrovei, minutum, octosporum*), *Thraustochytrium* (species include *arudimentale, aureum, benthicola, globosum, kinnei, motivum, multirudimentale, pachydermum, proliferum, roseum, striatum*), *Ulkenia* (species include *amoeboidea, kerguelensis, minuta, profunda, radiate, sailens, sarkariania, schizochytrops, visurgensis, yorkensis*), *Aplanochytrium* (species include *haliotidis, kerguelensis, profunda, stocchinoi*), *Japonochytrium* (spiecies include *marinum*), *Althornia* (species include *crouchii*), and *Elina* (species include *marisalba, sinorifica*). The Labrinthulids include the genera *Labyrinthula* (species include *algeriensis, coenocystis, chattonii, macrocystis, macrocystis atlantica, macrocystis macrocystis, marina, minuta, roscoffcnsis, valkanovii, vitellina, vitellina pacifica, vitellina vitellina, zopfi*), *Labyrinthomyxa* (species include *marina*), *Labyrinthuloides* (species include *haliotidis, yorkensis*), *Diplophrys* (species include *archeri*), *Pyrrhosorus\** (species include *marinus*), *Sorodiplophrys\** (species include *stercorea*), *Chlamydomyxa\** (species include *labyrinthuloides, montana*). (\*=there is no current general consensus on the exact taxonomic placement of these genera). While processes of the present invention can be used to produce forms of nutrients that can be produced in a wide variety of microorganisms, for the sake of brevity, convenience and illustration, this detailed description of the invention will discuss processes for growing microorganisms which are capable of producing lipids comprising omega-3 and/or omega-6 polyunsaturated fatty acids, in particular microorganisms that are capable of producing DHA, DPA n-3, DPA n-6, EPA or ARA. Additional preferred microorganisms are algae, such as Thraustochytrids of the order Thraustochytriales, including *Thraustochytrium* (including *Ulkenia*) and *Schizochytrium*, and including Thraustochytriales which are disclosed in commonly assigned U.S. Pat. Nos. 5,340,594 and 5,340,742, both issued to Barclay, all of which are incorporated herein by reference in their entirety. More preferably, the microorganisms are selected from the group consisting of microorganisms having the identifying characteristics of ATCC number 20888, ATCC number 20889, ATCC number 20890, ATCC number 20891 and ATCC number 20892. Since there is some disagreement among experts as to whether *Ulkenia* is a separate genus from the genus *Thraustochytrium*, for the purposes of this application, the genus *Thraustochytrium* will include *Ulkenia*. Also preferred are strains of strains of *Mortierella* sect. *schmuckeri* (e.g., including microorganisms having the identifying characteristics of ATCC 74371) and *Mortierella alpina* (e.g., including microorganisms having the identifying characteristics of ATCC 42430). Also preferred are strains of *Cryptheсodinium cohnii*, including microorganisms having the identifying characteristics of ATCC Nos. 30021, 30334-30348, 30541-30543, 30555-30557, 30571, 30572, 30772-30775, 30812, 40750, 50050-50060, and 50297-50300. Also preferred are mutant strains derived from any of the foregoing, and mixtures thereof. Oleaginous microorganisms are also preferred. As used herein, "oleaginous microorganisms" are defined as microorganisms capable of accumulating greater than 20% of the weight of their cells in the form of lipids. Genetically modified microorganisms that produce LC-PUFAs are also suitable for the present invention. These can include naturally LC-PUFA-producing microorganisms that have been genetically modified as well as microorganisms that do not naturally produce LC-PUFAs but that have been genetically engineered to do so.

Suitable organisms may be obtained from a number of available sources, including by collection from the natural environment. The American Type Culture Collection currently lists many publicly available strains of microorganisms identified above. As used herein, any microorganism, or any specific type of organism, includes wild strains, mutants, or recombinant types. Growth conditions in which to culture these organisms are known in the art, and appropriate growth conditions for at least some of these organisms are disclosed in, for example, U.S. Pat. No. 5,130,242, U.S. Pat. No. 5,407,957, U.S. Pat. No. 5,397,591, U.S. Pat. No. 5,492,938, U.S. Pat. No. 5,711,983, U.S. Pat. No. 5,882,703, U.S. Pat. No. 6,245,365, and U.S. Pat. No. 6,607,900, all of which are incorporated herein by reference in their entirety.

Microbial oils useful in the present invention can be recovered from microbial sources by any suitable means known to those in the art. For example, the oils can be recovered by extraction with solvents such as chloroform, hexane, methylene chloride, methanol and the like, or by supercritical fluid extraction. Alternatively, the oils can be extracted using extraction techniques, such as are described in U.S. Pat. No. 6,750,048 and PCT Patent Application Serial No. US01/01806, both filed Jan. 19, 2001, and entitled "Solventless Extraction Process," both of which are incorporated herein by reference in their entirety. Additional extraction and/or purification techniques are taught in PCT Patent Application Serial No. PCT/IB01/00841 entitled "Method for the Fractionation of Oil and Polar Lipid-Containing Native Raw Materials" filed Apr. 12, 2001; PCT Patent Application Serial No. PCT/IB01/00963 entitled "Method for the Fractionation of Oil and Polar Lipid-Containing Native Raw Materials Using Water-Soluble Organic Solvent and Centrifugation" filed Apr. 12, 2001; U.S. Provisional Patent Application Ser. No. 60/291,484 entitled "Production and Use of a Polar Lipid-Rich Fraction Containing Stearidonic Acid and Gamma Linolenic Acid from Plant Seeds and Microbes filed May 14, 2001; U.S. Provisional Patent Application Ser. No. 60/290,899 entitled "Production and Use of a Polar-Lipid Fraction Containing Omega-3 and/or Omega-6 Highly Unsaturated Fatty Acids from Microbes, Genetically Modified Plant Seeds and Marine Organisms" filed May 14, 2001; U.S. Pat. No. 6,399,803 entitled "Process for Separating a Triglyceride Comprising a Docosahexaenoic Acid Residue from a Mixture of Triglycerides" issued Jun. 4, 2002 filed Feb. 17, 2000; and PCT Patent Application Serial No. US01/01010 entitled "Process for Making an Enriched Mixture of Polyunsaturated Fatty Acid Esters" filed Jan. 11, 2001; all of which are incorporated herein by reference in their entirety. The extracted oils can be evaporated under reduced pressure to produce a sample of concentrated oil material. Processes for the enzyme treatment of biomass for the recovery of lipids are disclosed in U.S. Provisional Patent Application No. 60/377,550, entitled "HIGH-QUALITY LIPIDS AND METHODS FOR PRODUCING BY ENZYMATIC LIBERATION FROM BIOMASS," filed on May 3, 2002; PCT Patent Application Serial No. PCT/US03/14177 entitled "HIGH-QUALITY LIPIDS AND METHODS FOR PRODUCING BY ENZYMATIC LIBERATION FROM BIOMASS," filed on May 5, 2003; copending U.S. patent application Ser. No. 10/971,723, entitled "HIGH-QUALITY LIPIDS AND METHODS FOR PRODUCING BY LIBERATION FROM BIOMASS," filed on Oct. 22, 2004; EP Patent Publication 0 776 356 and U.S. Pat. No. 5,928,696, both entitled "Process for extracting native products which are not water-soluble from native substance mixtures by centrifugal force," the disclosures of which are hereby incorporated by reference herein in their entirety.

In preferred embodiments, the microbial crude oils of the invention are high quality microbial crude oils prepared by processes as described above. Such oils of the present invention have significant advantages over, for example, fish oils that typically provide poor quality crude oils, e.g., because recovery from fish biomass typically involves cooking and hexane extraction and because the oil can contain contaminants and/or other undesirable components and/or undesirable fatty acid profiles.

The microbial oil-containing fraction comprising at least one LC-PUFA, extracted from a microbial biomass as described above, includes at least one LC-PUFA (i.e., PUFAs having 20 or more carbons). Preferred PUFAs of the present invention include C20, C22, or C24 omega-3 or omega-6 PU-PUFAs. Preferably, the PUFA is a long chain PUFA (LC-PUFA), comprising a C20 or C22 omega-3, or a C20 or C22 omega-6 polyunsaturated fatty acid. An LC-PUFA of the present invention contains at least two double bonds and preferably, three double bonds, and even more preferably at least four double bonds. PUFAs having 4 or more unsaturated carbon-carbon bonds are also commonly referred to as highly unsaturated fatty acids, or HUFAs. In particular, the LC-PUFA can include docosahexaenoic acid (at least about 10, about 20, about 30, about 40, about 50, about 60, about 70 or about 80 weight percent of total fatty acids), docosapentaenoic acid n-3 (at least about 10, about 20, about 30, about 40, about 50, about 60, about 70 or about 80 weight percent of total fatty acids), docosapentaenoic acid n-6 (at least about 10, about 20, about 30, about 40, about 50, about 60, about 70 or about 80 weight percent of total fatty acids), arachidonic acid (at least about 10, about 20, about 30, about 40, about 50, about 60, about 70 or about 80 weight percent of total fatty acids) and/or eicosapentaenoic acid (at least about 10, about 20, about 30, about 40, about 50, about 60, about 70 or about 80 weight percent of total fatty acids). The PUFAs can be in any of the common forms found in natural lipids including but not limited to triacylglycerols, diacylglycerols, monoacylglycerols, phospholipids, free fatty acids, esterified fatty acids, or in natural or synthetic derivative forms of these fatty acids (e.g. calcium salts of fatty acids, ethyl esters, etc). In preferred embodiments, the microbial oil-containing fraction comprises at least about 70 wt. % of the PUFAs in the fraction in the triglyceride form, at least about 80 wt. %, at least about 90 wt. %, and at least about 95 wt. %. The term LC-PUFA, as used in the present invention, can refer to either an oil comprising a single omega-3 LC-PUFA such as DHA, an oil comprising a single omega-6 LC-PUFA such as ARA or DPA n-6, or an oil comprising a mixture of two or more LC-PUFAs such as DHA, DPA n-6, ARA, and EPA. In preferred embodiments, the product comprises an LC-PUFA in combination with at least one other nutrient.

In addition to the use of a microbial biomass for the extraction of oils, the present invention also includes the use of oil seeds as a biomass for extraction or recovery of LC-PUFAs. Such oils extracted from an oil seed biomass can be processed and treated as disclosed herein to produce oil products. For example, oil seeds from any higher plant, and particularly consumable plants, including crop plants and especially plants used for their oils. Such plants can include, for example: canola, soybeans, rapeseed, linseed, corn, safflowers, sunflowers and tobacco. Other preferred plants include those plants that are known to produce compounds used as pharmaceutical agents, flavoring agents, nutraceutical agents, functional food ingredients or cosmetically active agents or plants that are genetically engineered to produce these compounds/agents. Particularly preferred plants include plants that have been genetically modified to produce LC-PUFAs, such as plants into which genes for a polyketide synthase system have been introduced. For example, such genes and methods of plant transformation are disclosed in PCT Publication No. WO 02/083870 A2, PCT Publication No. WO 2004/087879 A2, PCT Publication No. WO 2000/42195 A2, US Patent Publication No. US-2005-0100995-A1, U.S. Provisional Patent Application Ser. No. 60/671,656, filed on Apr. 15, 2005, and US Patent Publication No. US-2005-0014231-A1, all of which are incorporated herein by reference.

Such seeds are treated by conventional methods to recover oils, such as by cleaning, dehulling and grinding. The seeds can then be pressed to produce an oil or contacted with a solvent, such as after flaking, to extract an oil. Suitable solvents can include organic solvents, water miscible solvents and water. A preferred solvent is hexane.

A further characteristic of PUFA-containing oil products in various embodiments of the invention is that they contain saturated fatty acids that are at least sufficient to visually affect the oil-containing fraction. Many PUFA-containing oil products contain sufficient amounts of saturated fatty acids in forms that, at room temperature (i.e., 20° C.), visually affect the oil, such as by causing cloudiness in the oil. Some such products are even paste-like due to the presence of saturated fatty acids, for example because they contain sufficient saturated fatty acids in the form of triglycerides. While in conventional processing, such oil products are winterized to remove the saturated fatty acids, the present invention recognizes that commercially valuable products can be prepared from such oil products without winterization as discussed in more detail below.

In preferred embodiments of the present invention, oils have a lipid profile particularly suitable for producing solid or semi-solid compositions comprising LC PUFAs. More particularly, such oils are relatively concentrated in highly unsaturated compounds (e.g., 4, 5 or higher points of unsaturation), relatively concentrated in saturated compounds, and/or relatively unconcentrated in mono-, di-, and tri-saturated compounds. Such compositions can be characterized as having a bimodal distribution of compounds in terms of saturation, i.e., high amounts of saturated compounds and high amounts of highly unsaturated compounds, with low amounts of compounds with intermediate amounts of unsaturatation. For example, such oils can have greater than about 20% by weight, greater than about 25% by weight, greater than about 30% by weight, greater than about 35% by weight, greater than about 40% by weight, greater than about 45% by weight, or greater than about 50% by weight of highly unsaturated compounds having 4 or more points of unsaturation. In other embodiments, such oils can have greater than about 20% by weight, greater than about 25% by weight, greater than about 30% by weight, greater than about 35% by weight, greater than about 40% by weight, greater than about 45% by weight, or greater than about 50% by weight of highly unsaturated compounds having 5 or more points of unsaturation. Alternatively or in addition, such oils can have greater than about 30% by weight, greater than about 35% by weight, greater than about 40% by weight, greater than about 45% by weight, or greater than about 50% by weight of saturated compounds. Alternatively or in addition, such oils can have less than about 25% by weight, less than about 20% by weight, less than about 15% by weight, less than about 10% by weight, or less than about 5% by weight of mono-, di- or tri-saturated compounds.

A process of the invention for producing minimally processed high-quality PUFA-containing oil products comprising at least one LC-PUFA further includes treating the extracted oil-containing fraction produced as described above. Such further treatment includes a process of vacuum evaporation to produce an oil product comprising at least one LC-PUFA.

The process of desolventization or drying by high vacuum evaporation is generally known in the art and includes subjecting an extracted oil to vacuum conditions, preferably at high temperatures (e.g., from about 50° C. to about 70° C.). For example, the oil can be subjected to a vacuum of greater than a vacuum of about 100 mm Hg, greater than a vacuum of about 70 mm Hg, and greater than a vacuum of about 50 mm Hg. As used herein, for example, reference to "to a vacuum of greater than a vacuum of about 100 min Hg" means a stronger vacuum such as, e.g., a vacuum of 90 mm Hg or 80 mm Hg. Under these conditions, any solvents, water or other components in the extracted oil having a boiling point below the oil will be driven off.

The process of deodorization is generally known in the art and includes subjecting an extracted oil to vacuum conditions to remove any low molecular weight components that may be present. Typically, these components are removed by sparging with steam at high temperatures, under high vacuum. For example, the oil is generally subjected to vacuums greater than those noted above for desolventization. Specifically, the vacuum can be a vacuum of greater than a vacuum of about 50 min Hg, greater than a vacuum of about 25 mm Hg, greater than a vacuum of about 12 mm Hg, greater than a vacuum of about 6 mm Hg, and typically can be between a vacuum of about 12 mm Hg and a vacuum of about 6 mm Hg or be between a vacuum of about 6 min Hg and a vacuum of about 1 mm Hg. This process also destroys many peroxide bonds that may be present and reduces or removes off odors and helps improve the stability of the oil. In addition, under these conditions, solvents, water or other components in the extracted oil having a boiling point below the oil will be driven off. Deodorization is typically performed at high temperatures, such as temperatures between about 190° C. and about 220° C.

The oil product resulting from this process is a high-quality PUFA-containing oil that is used for or suitable for consumption by humans and non-human animals. That is the organoleptic properties of the oil are such that consumption of the product is acceptable to humans and non-human animals. Specifically, the oil product can contain low concentrations of free fatty acids, phosphorous, peroxide values, anisidine values, soaps and heavy metals. Production of this oil by the present invention minimizes the amount of downstream processing required to bring a microbial oil to acceptable commercial conditions. Specific modifications include the elimination of a solvent winterization step, the elimination of a caustic refining process, the elimination of a chill filtration process, and the possible elimination of a bleaching process. In addition, a high-vacuum evaporation process can be substituted for a deodorization process. The foregoing process description facilitates the production of a solid or semi-solid product by retaining the presence of sufficient saturated compounds to prevent the composition from being liquid at room temperature (i.e., about 20° C.). The invention allows production of edible oils from crude microbial oils with exceptionally high recoveries (95-100%) that are compatible with the natural and/or organic market sector.

In various embodiments, oil products of the present invention, such as oils produced without being subjected to one or more of the conventional processing steps of solvent winterization, caustic refining process, chill filtration process, and a bleaching process, have low concentrations of free fatty acids. Measurement of concentrations of free fatty acids of oils is well known in the art. More particularly, oils of the invention can have a free fatty acid content of less than about 0.5 wt. %, less than about 0.1 wt. %, and less than about 0.05 wt. %.

In various embodiments, oil products of the present invention, such as oils produced without being subjected to one or more of the conventional processing steps of solvent winterization, caustic refining process, chill filtration process, and a bleaching process, have low phosphorous values. Measurement of phosphorous values of oils is well known in the art. More particularly, oils of the invention can have a phosphorous value of less than about 10 ppm, less than about 5 ppm, and about 0 ppm.

In various embodiments, oil products of the present invention, such as oils produced without being subjected to one or more of the conventional processing steps of solvent winterization, caustic refining process, chill filtration process, and a bleaching process, have low peroxide values. Measurement of peroxide values of oils is well known in the art. More particularly, oils of the invention can have an peroxide value of less than about 2 meq/kg, less than about 1 meq/kg, and about 0 meq/kg.

In various embodiments, oil products of the present invention, such as oils produced without being subjected to one or more of the conventional processing steps of solvent winterization, caustic refining process, chill filtration process, and a bleaching process, have low anisidine values. Measurement of anisidine values of oils is well known in the art. More particularly, oils of the invention can have an anisidine value of less than about 5, less than about 3, less than about 2, less than about 1, less than about 0.5, less than about 0.3, less than about 0.1, and below detection.

In various embodiments, oil products of the present invention, such as oils produced without being subjected to one or more of the conventional processing steps of solvent winterization, caustic refining process, chill filtration process, and a bleaching process, have low concentrations of soaps. Measurement of concentrations of soap of oils is well known in the art. More particularly, oils of the invention can have soap contents of less than about 5 wt. %, less than about 2.5 wt. %, and of 0 wt. %.

In various embodiments, oil products of the present invention, such as oils produced without being subjected to one or more of the conventional processing steps of solvent winterization, caustic refining process, chill filtration process, and a bleaching process, have low heavy metal values. Measurement of heavy metal values of oils is well known in the art. More particularly, oils of the invention can have Fe concentrations of less than about 1 ppm, less than about 0.5 ppm, and preferably at about 0 ppm; Pb concentrations of less than about 1 ppm, less than about 0.2 ppm, and preferably at about 0 ppm; Hg concentrations of less than about 0.1 ppm, less than about 0.04 ppm, and preferably at about 0 ppm; Ni concentrations of less than about 0.1 ppm, less than about 0.01 ppm, and preferably at about 0 ppm; Cu concentrations of less than about 1 ppm, less than about 0.2 ppm, and preferably at about 0 ppm.

Processes of the present invention to produce minimally processed high-quality PUFA-containing oil products having at least one LC-PUFA can optionally include a step of bleaching the oil product either before or after the step of deodorization or the step of high vacuum fractionation, although it is more commonly conducted before the step of deodorization. Bleaching of oils is well known in the art and can be accomplished in conventional processes. Specifically, for example, a silica adsorbent (such as, Trysil 600 (Grace Chemicals)) for removing remnant soap and a bleaching clay can be introduced to the oil and then filtered out. Typically, the silica adsorbent is added before the bleaching clay.

Processes of the present invention to produce high-quality PUFA-containing oil products having at least one LC-PUFA can include a process to produce a liquid LC PUFA-containing oil fraction and an LC PUFA-containing solid fat product. Such a process includes a step of fractionating a high quality microbial crude oil, as disclosed herein, into an oil product and related solid fat product. Such crude oil products can be prepared by extracting an oil-containing fraction containing at least one LC-PUFA and saturated fatty acids from a microbial biomass. The oil-containing fraction can be treated by winterization, chill filtration, vacuum evaporation and/or other means to produce a liquid oil product comprising at least one LC-PUFA and a solid product comprising at least one LC-PUFA. Such other means can include filtration to separate the liquid oil fraction from a solid composition.

The solid fraction components (possibly including adsorbents) can be recovered by solid/liquid separation techniques. Any adsorbents can be separated from the solid fraction by heating the adsorbents and solid fat material to melt the solid fat material. The adsorbents can then be separated from the melted solids, by filtering, for example, and the melted solids can then be resolidified by cooling.

The recovered solid fraction will contain a high level of LC PUFA. In preferred embodiments, the solid fraction will comprise at least about 20%, at least about 25%, at least about 30% by weight LC PUFA and in particular DHA. Each of the clear oil and the solid can be used as a food or food additive, for example.

Oil products produced in accordance the present invention can be a solid or semi solid materials. As used herein, the term "oil" will include those materials that are solid or semi solid at room temperature, as well as those materials that are liquid at room temperature.

Processes of the present invention to produce minimally processed high-quality PUFA-containing oil products having at least one LC-PUFA can optionally include a step of fractionating the oil into an olein fraction and a stearin fraction after either the step of deodorization or the step of high vacuum fractionation. Fractionation of oils into olein and stearin fractions can be applied to any crude, or bleached or deodorized oil to produce a clear olein fraction and a hard stearin fraction. Due to differences in their physical properties, olein and stearin can be used in different food applications. In conventional processes, stearin is a byproduct of miscella winterization and chill filtration and is disposed of resulting in ~30% losses. Fractionation allows production of a saleable stearin fraction. An example of this fractionation is shown below in Example 5.

With reference to FIG. 1, various alternative embodiments of the present invention are illustrated. A starting material, such as a biomass, such as a spray dried biomass can be subjected to treatment by a solvent for extraction of a crude oil. Such crude oils will include long chain polyunsaturated fatty acids. The crude oil can be subjects to high vacuum evaporation which will remove extraction solvents, water and other components in the crude oil having a lower boiling point than the desired oil components. Alternatively, the crude oil can be subjected to an optional bleaching step, such as to remove carotenoids. The optionally treated crude oil is then subjected to deodorization by sparging the oil with steam at high temperatures, under high vacuum. The final oil product produced by either the high vacuum evaporation or the deodorization can then be optionally treated by fractionation into an olein fraction and a stearin fraction.

Figure 2:
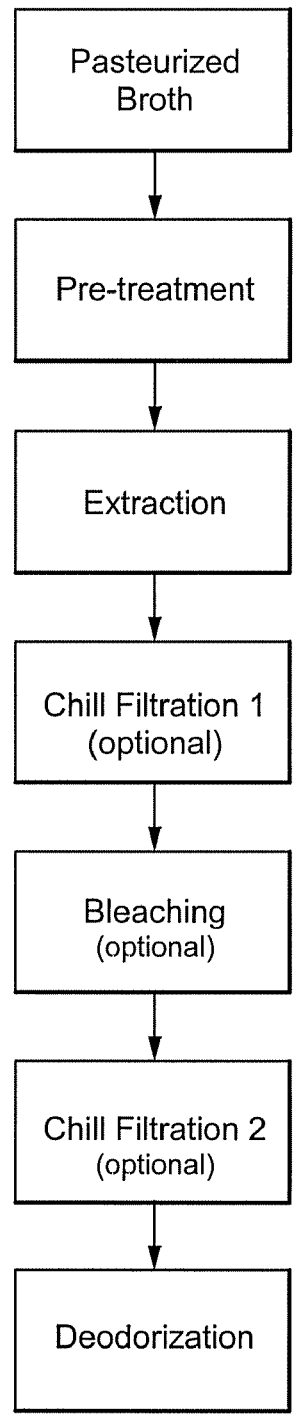
FIG. 2 illustrates various alternative embodiments of the present invention for producing a PUFA-containing oil of the present invention.

With reference to FIG. 2, various alternative embodiments of the present invention are illustrated by a flow sheet. In its most basic form, the process must include the steps of starting with a pasteurized fermentation broth containing a microbial biomass. The broth is pretreated to release oil from the cells by lysing, such as by enzymatic treatment or mechanical disruption. The pretreated fermentation broth is then subjected to an extraction step to produce a microbial oil. At a minimum, the process then includes a deodorization step as described herein. In one alternative process, the process includes a bleaching step by which the extracted microbial oil is subjected to bleaching prior to the step of deodorization. In further alternative embodiments, winterization steps (i.e., chill filtration) can be conducted on the extracted microbial oil prior to the step of bleaching and/or between the step of bleaching and deodorization.

Processes for producing minimally processed oils of the present invention and the resulting products have a number of significant advantages. Compared to conventional methods of producing PUFA-containing oil products, the present invention has a lower cost, reduced processing requirements, increased manufacturing throughput, increased safety of the processing steps, and eliminates waste/byproduct streams. Moreover, the current process is consistent with the natural and/or organic market sector. Conventional methods of oil processing typically utilize all facets of downstream processing, including chemical refining. Physical refining methods (i.e., methods that do not involve caustic refining) have not been extended to fish oil and similar PUFA-containing oils, possibly because of the known difficulties in the processing of such oils. Moreover, many of the known physical processing methods or less refined products are limited because of odor and taste limitations. Surprisingly, the process of the invention produces better tasting oils using physical methods and minimum steps.

As described more fully below, the high quality PUFA-containing oil products of the present invention can be used in a variety of food products and applications. The oil products can be consumed directly by humans as a nutritional, dietary, medicinal, or pharmaceutical product. In addition, the oil products can be combined with any known human food or liquid for consumption by humans to improve nutrition. The oil products can also be fed to animals directly as a feed or as a supplement to animal feed. In this manner, any animal-based food products can have enhanced quality when consumed by humans.

In one embodiment, the oil products of the present invention can be used to supplement infant formula. Infant formula can be supplemented with, for example, a physically refined oil derived from an ARA-producing microorganism such as *Mortierella alpina* or *Mortierella* sect. *schmuckeri*, either alone or in combination with other oils such as fish oil or additional oils rich in DHA, such as microbial oils, including DHA-S™ and DHA-T™ oils (Martek Biosciences, Columbia, Md.). Such physically refined ARA-containing oils would not have been chemically refined. Alternatively, infant formula can be supplemented with, for example, a minimally processed oil derived from a DHA-producing microorganism, such as *Crypthecodinium cohnii*, either alone or in combination with other oils rich in ARA including ARASCO® (Martek Biosciences, Columbia, Md.). In an additional embodiment, infant formula can be supplemented with multiple oils of the present invention that are derived from more than one source such as, for example, a minimally processed oil containing DHA (e.g., from *Crypthecodinium cohnii*) and a physically refined oil containing ARA (e.g., from *Mortierella alpina*).

In other embodiments, the oil products of the present invention can be combined to produce a blend. For example, a minimally processed oil from *Crylpthecodinium cohnii* can be blended with a physically refined oil from *Mortierella alpina* and the resulting blend can be used to supplement infant formula. Blends of ARA-containing oils and DHA-containing oils using oils of the present invention can be produced in a variety of different ratios of ARA to DHA. Such blends can include ratios of ARA:DHA from about 1:1 to about 2:1. More particularly, the blends can be produced having ARA:DHA ratios of about 1:1, 1.25:1, 1.5:1, 1.75:1 or 2:1.

In a particularly preferred embodiment, the high quality PUFA-containing oil products of the present invention can be used as a starting material for the solid fat compositions that are described in detail below. It should be appreciated, however, that use of the minimally processed oil products of the invention is not limited to a starting material for the solid fat composition that is described herein.

The inventors have surprisingly discovered that in preferred embodiments of the solid fat composition of the present invention, an unwinterized form of an LC-PUFA rich oil, including an unwinterized microbially-derived docosahexaenoic acid-containing oil (DHA oil), can be used as a starting material for the solid fat compositions of the present invention. The processes for making such compositions thereby can avoid the need for hydrogenation of oils, mixing these oils with hard or saturated fats, or other thickening-type agents. Typically, refined oils, i.e., liquid fish oils or microbial oils are produced as an initial crude oil that is then subjected to refining (which removes phospholipids and free fatty acids) and bleaching (to remove pigments) steps. The oil is then typically winterized to remove saturated fats.

The inventors have surprisingly found that, for example, an inwinterized microbial oil, i.e., where the winterization step is not performed, provides a starting material that does not require the treatments taught in the prior art to form a solid composition. In addition, unwinterized oil seed oils, as described above, can be used as an alternative to microbial oils as described below. Without being bound by theory, the inventors believe that the saturated fats present in the unwinterized oil gives a more solid consistency to the oil (as compared to winterized liquid oil). The methods of the present invention for producing a solid fat composition also overcome the tendency of an unwinterized oil to appear grainy (due to the crystallization of triglycerides) causing such unwinterized oils to appear like a thick liquid oil with particles. Upon standing at room temperature, unwinterized oil separates, giving a product that appears as a thick liquid oil with solids in it. The present invention can overcome this characteristic of unwinterized oil. Processes of the present invention, produce a smooth product of uniform appearance that is stable (with no apparent separation) when left standing at room temperature. The resulting product can have the consistency of shortening.

In a further embodiment, the present invention includes a method for producing a solid fat composition. The method includes the step of mixing an oil that includes saturated fat and a microbial oil with at least one LC-PUFA with at least one emulsifier to form a mixture. The mixture is then solidified to form a solid fat composition.

A "solid fat composition" refers a composition that is solid, or semi-solid, at room temperature (i.e., 20° C.). Physicochemical properties of fats and oils include their viscosity and melting temperature. Preferably, a solid fat composition will have a melting temperature of at least about 20° C., at least about 25° C., at least about 30° C. and preferably at least about 35° C. Melting temperatures will vary in their sharpness depending on the number of different chemical entities that are present. Typically, a mixture of several triglycerides has a lower melting point than would be predicted based on the melting points of the individual triglycerides. The mixture will also have a broader melting range than that of its individual components. Monoglycerides and diglycerides have higher melting points than triglycerides of similar fatty acid composition. In preferred embodiments, the solid fat composition will remain soft enough to spread onto food products. Preferably, at room temperatures, the composition will be viscous, have retarded flow properties, and/or be more adherent to surfaces than the starting materials from which the product is made.

The oil used in methods of the invention to produce a solid fat composition includes a microbial oil with at least one LC-PUFA. Microbial sources and methods for growing microorganisms comprising nutrients and/or LC-PUFAs for recovery in microbial oils are known in the art as described in detail above in the description of the minimally processed oils of the present invention. Such microbial sources and methods are suitable as well for producing microbial oils as a starting material for the solid fat compositions of the present invention. Indeed, minimally processed oils as described above are a preferred starting material for production of solid fat compositions. It should be appreciated, however, that a wide variety of other microbial oil starting materials, as described below, can be used as starting materials for solid fat compositions of the present invention. In one particularly preferred embodiment, the microbial oil is an oil produced according to the disclosures in PCT Patent Application Serial No. PCT/IB01/00841 entitled "Method for the Fractionation of Oil and Polar Lipid-Containing Native Raw Materials" filed Apr. 12, 2001, published as WO 01/76715 and PCT Patent application Ser. No. PCT/IB01/00963 entitled "Method for the Fractionation of Oil and Polar Lipid-Containing Native Raw Materials Using Water-Soluble Organic Solvent and Centrifugation" filed Apr. 12, 2001, published as WO 01/76385.

Disclosures in these two PCT applications describe a microbial oil recovery process that can be generally referred to as the Friolex process.

The microbial oil of the invention includes at least one LC-PUFA (i.e., PUFAs having 20 or more carbons). Preferred PUFAs of the present invention include C20, C22, or C24 omega-3 or omega-6 PUFAs. Preferably, the PUFA is a long chain PUFA (LC-PUFA), comprising a C20 or C22 omega-3, or a C20 or C22 omega-6 polyunsaturated fatty acid. An LC-PUFA of the present invention contains at least two double bonds and preferably, three double bonds, and even more preferably at least four double bonds. PUFAs having 4 or more unsaturated carbon-carbon bonds are also commonly referred to as highly unsaturated fatty acids, or HUFAs. In particular, the LC-PUFA can include docosahexaenoic acid (at least about 10, about 20, about 30, about 40, about 50, about 60, about 70 or about 80 weight percent of total fatty acids), docosapentaenoic acid n-3 (at least about 10, about 20, about 30, about 40, about 50, about 60, about 70 or about 80 weight percent of total fatty acids), docosapentaenoic acid n-6 (at least about 10, about 20, about 30, about 40, about 50, about 60, about 70 or about 80 weight percent of total fatty acids), arachidonic acid (at least about 10, about 20, about 30, about 40, about 50, about 60, about 70 or about 80 weight percent of total fatty acids) and/or eicosapentaenoic acid (at least about 10, about 20, about 30, about 40, about 50, about 60, about 70 or about 80 weight percent of total fatty acids). The PUFAs can be in any of the common forms found in natural lipids including but not limited to triacylglycerols, diacylglycerols, monoacylglycerols, phospholipids, free fatty acids, esterified fatty acids, or in natural or synthetic derivative forms of these fatty acids (e.g. calcium salts of fatty acids, ethyl esters, etc). In preferred embodiments, the microbial oil comprises at least about 70 wt. % of the PUFAs in the oil in the triglyceride form, at least about 80 wt. %, at least about 90 wt. %, and at least about 95 wt. %. The term LC-PUFA, as used in the present invention, can refer to either an oil comprising a single omega-3 LC-PUFA such as DHA, an oil comprising a single omega-6 LC-PUFA such as ARA or DPA n-6, or an oil comprising a mixture of two or more LC-PUFAs such as DHA, DPA n-6, ARA, and EPA. In preferred embodiments, the product comprises an LC-PUFA in combination with at least one other nutrient.

In preferred embodiments of the invention, the oil used in methods of the invention to produce a solid fat composition can include at least about 5 wt. %, at least about 10 wt. %, at least about 15 wt. %, at least about 20 wt. % of LC-PUFA, at least about 25 wt. %, at least about 30 wt. %, at least about 35 wt. % of LC-PUFA, at least about 40 wt. %, at least about 45 wt. %, and at least about 50 wt. % of LC-PUFA. Such embodiments can also have less that about 30 wt. %, less than about 35 wt. %, less than about 40 wt. % less than about 45 wt. % LC-PUFA, less that about 50 wt. %, less than about 55 wt. %, less than about 60 wt. %, less than about 65 wt. % LC-PUFA, and less than about 70 wt. % LC-PUFA.

The oil used in methods of the invention to produce a solid fat composition, in addition to a microbial oil with at least one LC-PUFA, includes saturated fat. Saturated fats will typically have a higher melting point than the LC-PUFA or mixture of LC-PUFAs. Such a saturated fat can be added to the oil exogenously. Preferred exogenously added saturated fats to add include "hard fats" such as partially hydrogenated vegetable oils, fully hydrogenated oils, partially hydrogenated lards, and non-trans tropical oils. For example, palm oil and palm kernel oil and fractions thereof (palm and palm kernel olein and palm and palm kernel stearin) can be used. When the composition includes an exogenously added fat, the LC-PUFA oil may or may not be winterized. A preferred amount of exogenously added fat can be determined by one of skill in the art depending on the degree of solidity and/or viscosity of the starting material and the desired degree of solidity and/or viscosity and/or spread consistency desired in the composition. Exogenously added fats can be added in amounts of from about 20 wt. % to about 60 wt. %, from about 30 wt. % to about 50 wt. %, and from about 35 wt. % to about 45 wt. %.

In preferred embodiments, the saturated fat is not added exogenously, but occurs naturally in the microbial oil. For example, microbial oils comprising LC-PUFAs may be unprocessed oils extracted by any means known in the art. In such oils, the amount of saturated fats in the microbial oil can be from about 20 wt. % to about 60 wt. %, from about 30 wt. % to about 50 wt. %, and from about 35 wt. % to about 45 wt. %.

In preferred embodiments of the present invention, the microbial oil is unwinterized (i.e., unfractionated) and will therefore contain saturated fats. Winterization refers to the process of removing sediment (typically, high melting solid saturated fats) that appears in many oils, including vegetable oils, at low temperature, most typically involving the removal of the quantity of crystallized material by filtration to avoid clouding of the liquid fractions at refrigerator temperatures. Such techniques include separating oils into two or more fractions with different melting points. The separated liquid and solid fractions exhibit significant differences in physical and chemical properties. Suitable techniques are known in the art, and typically include the following three steps: (i) cooling of the liquid oil to supersaturation, resulting in the formation of nuclei for crystallization, (ii) progressive growth of the crystals by gradual cooling, and (iii) separation of the liquid and crystalline phases. These techniques can include, for example, conventional winterization, detergent fractionation and solvent winterization. Conventional winterization includes dry fractional crystallization wherein triglycerides with the highest melting temperature preferentially crystallize during cooling from the neat liquid or melted fat. The principle of dry fractionation process is based on the cooling of oil under controlled conditions without the addition of chemicals. The liquid and solid phases are separated by mechanical means. The principle of detergent fractionation is similar to dry fractionation based on the cooling of oil under controlled conditions without the addition of a solvent. Subsequently, the liquid and solid phases are separated by centrifugation after an aqueous detergent solution has been added. Solvent (typically acetone) winterization is used to promote triglyceride crystal formation, because triglycerides at low temperature generally form more stable crystals with solvent than without solvent. In solvent-aided fractionation, either polar or non-polar solvents may be used to reduce the viscosity of the system during filtration. The fractions obtained are then freed from the solvent by distillation. Thus, unwinterized microbial oils are those that have not been subjected to a winterization or fractionation process.

In further preferred embodiments, the microbial oil is not hydrogenated nor partially hydrogenated. Hydrogenation is known in the art, and includes processes of chemically adding hydrogen gas to a liquid fat in the presence of a catalyst. This process converts at least some of the double bonds of unsaturated fatty acids in the fat molecules to single bonds thereby increasing the degree of saturation of the fat. The degree of hydrogenation, that is the total number of double bonds that are converted, determines the physical and chemical properties of the hydrogenated fat. An oil that has been partially hydrogenated often retains a significant degree of unsaturation in its fatty acids. Hydrogenation also results in the conversion of some cis double bonds to the trans configuration in which one or more double bonds has migrated to a new position in the fatty acid chain. Current studies indicate that trans-fatty acids may raise total cholesterol and heart disease risk to about the same extent as saturated fatty acids and are therefore, undesirable in the diet. The present invention allows for the formation of a solid or semi-solid product without the necessity for hydrogenation or partial hydrogenation. The present method includes mixing at least one emulsifier with the oil including a microbial oil having at least one LC-PUFA. Preferred emulsifiers to use with the present invention a monoglyceride, a diglyceride, a mono/diglyceride combination, a lecithin, a lactylated mono-diglyceride, a polyglycerol ester, a sucrose fatty acid ester, sodium steroyl lactylate, calcium steroyl lactylate, and combinations thereof. In a preferred embodiment, the emulsifier is a mono/diglyceride combination. In a preferred embodiment, the emulsifier is present in the mixture in an amount of between about 0.01 weight percent and about 2.0 weight percent, in an amount of between about 0.025 weight percent and about 1.0 weight percent, and in an amount of between about 0.05 weight percent and about 0.2 weight percent. Without intending to be bound by theory, it is thought that an emulsifier may act to provide stability between various components in the mixture to maintain a homogeneous composition. Lack of stability may result in separation of oils or separation of the oil and a water phase. Emulsifiers may also provide functional attributes in addition to emulsification, which include aeration, starch and protein complexing, hydration, crystal modification, solubilization, and dispersion.

The physical step of mixing the emulsifier with the oil is conducted in any conventional manner of mixing known in the art. The compositions are mixed to achieve mixing, such as to achieve a homogeneous liquid solution. For example, it may be necessary to heat the microbial oil and/or the emulsifier, e.g., to at least about 40° C., so that the compositions are completely liquid and miscible in each other. In a preferred embodiment, the oil is an unwinterized LC-PUFA rich oil and is heated to at least about 40° C. to solubilize all components of the oil. The emulsifier is, in a preferred embodiment, a mixture of mono and diglyceride emulsifers that are heated to form a liquid in a separate container from the oil. The melted oil and emulsifier are then mixed together by any known method, preferably by agitation to form a continuous mixture.

The present method also includes solidifying the mixture of the oil and the emulsifier to form a solid fat composition. For example, in a preferred embodiment in which the mixture is above room temperature, the mixture can be allowed to cool to room temperature. Alternatively, the mixture can be actively cooled to room temperature or for example, below room temperature. For example, the composition can be cooled to between about 0° C. to about 3° C. to solidify. During the step of cooling, whether active or passive, the mixture can be mixed or agitated. In this manner, cooling can be controlled so that uniform cooling is achieved without creating a stratified composition. Preferably, such cooling conditions are adjusted in order to allow the crystal structure of the fat (i.e., the manner in which the molecules orient themselves in the solid stage) to reach desired levels resulting in desired product plasticity, functionality, and stability. In general, β-prime crystals result in a smooth, creamy consistency. β crystals are typically larger, coarser and grainier than β-prime crystals, and accordingly, are typically less desirable. Accordingly, in preferred embodiments, the cooling process is controlled so as to allow triglycerides in the mixture to reach stable, β-prime configurations to produce a product having a smooth consistency. Methods to cool that allow such preferred crystallization forms include cooling the mixture at a rate of between about 1° C./min and about 20° C./min, between about 5° C./min and about 15° C./min, and at about 10° C./min. Without being bound by theory, the inventors believe that some emulsifiers suitable for use with the present invention, such as mono and diglycerides, act to at least partially influence and/or control triglyceride crystallization in the composition to result in β-prime crystals. Preferably, at least about 50 wt. % of the fats and/or oils in the solid fat composition, at least about 55 wt. %, at least about 60 wt. %, at least about 65 wt. %, at least about 70 wt. %, at least about 75 wt. %, at least about 80 wt. %, at least about 85 wt. %, at least about 90 wt. %, at least about 95 wt. %, or about 100 wt. % are in the β-prime crystal configuration.

In further embodiments, the step of solidifying the mixture of the oil and the emulsifier to form a solid fat composition can include introducing nitrogen through the mixture. For example, nitrogen can be bubbled into the composition. Alternatively, nitrogen can be introduced along with the emulsion into a low temperature crystallizer.

The introduction of nitrogen during solidification can enhance oxidative stability of the product and can improve the product appearance by providing a shiny appearance.

In preferred embodiments, the solid fat composition of the present invention has a homogeneous texture and therefore, has a uniform appearance and consistency. Another characteristic of these embodiments is that the composition is stable, and does not separate upon standing or otherwise lose its homogeneous texture, preferably for extended periods of time. Thus, the composition does not develop a non-uniform appearance or consistency upon standing. In preferred embodiments, the composition of the present invention can stand at least about one day, at least about one week, at least about two weeks, at least about three weeks, and at least about four weeks at room temperature without separating or otherwise losing its homogeneous texture.

The composition of the present invention can also include a number of additional functional ingredients. For example, the compositions of the present invention can further include microencapsulants including, for example, proteins, simple and complex carbohydrates, solids and particulates. Preferred microencapsulants include cell particulates, gum acacia, maltodextrin, hydrophobically modified starch, polysaccharides, including alginate, carboxymethylcellulose and guar gum, hydrophobically-modified polysaccharides, such as octyl-substituted starches, proteins, including whey protein isolates, soy proteins, and sodium caseinate, and combinations thereof. In addition, compositions of the invention can include surfactants, including for example, anionic agents, cationic agents, nonionic agents, amphoteric agents, water-insoluble emulsifying agents, finely divided particles and naturally occurring materials. Anionic agents include carboxylic acids, sulfuric esters, alkane sulfonic acids, alkyl aromatic sulfonic acids, miscellaneous anionic hydrophilic groups; cationic agents include amine salts, ammonium compounds, other nitrogenous bases, non-nitrogenous bases; nonionic agents include an ether linkage to solubilizing group, ester linkage, amide linkage, miscellaneous linkage, multiple linkages; amploteric agents include amino and carboxy, amino and sulfuric esters, amino and alkane sulfonic acids, amino and aromatic sulfonic acids, miscellaneous combinations of basic and acidic groups; water insoluble emulsifying agents include ionic hydrophilic groups, non-ionic hydrophilic groups; finely divided particles include any finely divided non-solubilized particle including clays and carbon; naturally occurring materials include alginates, cellulose derivatives water-soluble gums, lipids and sterols, phospholipids, fatty acids, alcohols, proteins, amino acids, detergents; and hydrophilic colloids. Other optional ingredients include thickening agents that include polysaccharides. Thickeners are ingredients that are used to increase the viscosity of the composition. In such embodiments, the additional functional ingredient(s) are typically added during the step of mixing.

In one embodiment, the solid fat composition is a shortening. Shortenings typically have little to no added water or aqueous component and comprise high levels of fats. Alternatively, the solid fat composition can be a product such as a margarine, spread, mayonnaise, or salad dressing. Such products are prepared by blending fats and/or oils with other ingredients such as water and/or milk products, suitable edible proteins, salt, flavoring and coloring materials and Vitamins A and D. Margarine typically contains at least 80% fat. Mayonnaise and salad dressing are semi-solid fatty foods that typically contain not less than 65% and 30% vegetable oil, respectively, and dried whole eggs or egg yolks. Salt, sugar, spices, seasoning, vinegar, lemon juice, and other ingredients complete these products.

Accordingly, the compositions of the present invention can further include the presence of or the addition of a water-soluble liquid to the mixture. Preferably, the water-soluble liquid is water and is added in an amount of less than about 10 wt. %, between about 1 wt. % and about 10 wt. %, between about 2 wt. % and about 8 wt. %, and between about 4 wt. % and about 6 wt. %. The presence of a water-soluble liquid allows for the addition of one or more additional water-soluble ingredients. Any water-soluble ingredient is suitable for the present invention. A preferred additional ingredient includes antioxidants, flavors, flavor enhancers, sweeteners, pigments, vitamins, minerals, pre-biotic compounds, pro-biotic compounds, therapeutic ingredients, medicinal ingredients, functional food ingredients, processing ingredients, and combinations thereof.

In a particularly preferred embodiment, the additional ingredient is an antioxidant. Antioxidants are known in the art, and may be added at any point in the production of the microbial oil by fermentation or lipid processing, or during the processes of the present invention. Antioxidants can help to preserve the resulting products from oxidative deterioration. Suitable antioxidants may be chosen by the skilled artisan. Preferred antioxidants include ascorbyl palmitate, tocopherols, citric acid, ascorbic acid, tertiary butyl hydroquinone (TBHQ), rosemary extract, lecithin, and mixtures thereof. Antioxidants can be included in products in amounts that are conventional in the art. Particularly preferred antioxidants include ascorbic acid or a salt of ascorbic acid. In preferred embodiments, when the antioxidant is ascorbic acid or a salt of ascorbic acid, it can be added in amounts up to about 5 wt. %, including amounts ranging from about 0.5 wt. % to about 5 wt. %, from about 1.5 wt. % to about 5 wt. %, and from about 3 wt. % to about 5 wt. %. It should be noted that when a water soluble antioxidant, such as ascorbic acid, citric acid or salts thereof is added, it must be added with water so that it is well dispersed in the composition. Surprisingly, it has been found that the level of increase in the oxidative stability of products of the present invention is greater than expected for the amount of antioxidant used, and in particular, when the antioxidant is ascorbic acid or a salt of ascorbic acid. For example, the addition of about 5 wt. % of ascorbic acid or its salt increases the OSI (oxidative stability index) of a composition of the present invention three-fold.

The oxidative state and stability of a composition including a lipid may be measured in a number of ways known in the art, and descriptions of many of these techniques are available from the American Oil Chemist's Society, as well as from other sources. One method of quantifying the oxidative stability of a product is by measuring the Oxidative Stability Index (OSI), such as by use of a Rancimat instrument, that measures the amount of conductive species (volatile decomposition products) that are evolved from a sample as it is subjected to thermal decomposition. In preferred embodiments, compositions of the present invention have OSI values of at least about 10, at least about 20, at least about 30, at least about 40, at least about 50, and at least about 60.

In preferred embodiments, the products of the present invention (including the high quality PUFA-containing oil products and the solid fat compositions) are stored under appropriate conditions to minimize oxidative degradation. Many methods to effect such storage conditions are known in the art and are suitable for use with the present invention, such as, for example, replacement of ambient air with an inert gas atmosphere. A preferred method by which to reduce or minimize oxidative degradation is to store products under a nitrogen ($N_2$) atmosphere or mixed nitrogen and carbon dioxide atmosphere. Preferably, packaged products are packaged under nitrogen. Methods for producing a nitrogen gas atmosphere into a container comprising a product are known in the art. In other preferred embodiments, oxidative and/or chemical stability of this product can also be increased by bubbling nitrogen into the mixture as it is cooling to provide extra protection against oxidation.

In another preferred embodiment, products of the present invention can comprise a pharmaceutically acceptable excipient and/or an added pharmaceutically active agent (i.e., a therapeutically or medicinally active ingredient or combinations thereof). This embodiment is particularly advantageous for pharmaceutically active agents that have low solubility in water. Such pharmaceutical products have the advantage of providing therapeutically active ingredients together with beneficial nutrients such as LC-PUFAs. Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Pharmaceutically active agents of the present invention include, without limitation, statins, anti-hypertensive agents, anti-diabetic agents, anti-dementia agents, anti-depressants, anti-obesity agents, appetite suppressants and agents to enhance memory and/or cognitive function. In another preferred embodiment, products of the present invention can comprise food ingredients such as functional food ingredients, food additives or other ingredients.

The products of the present invention can be used alone as a food product, nutritional product, or pharmaceutical product, or may be incorporated or added to a food, nutritional, or pharmaceutical product. In a first embodiment, the product of the invention is a food product that includes an oil product of the present invention and a food component. The products can be used directly as a food ingredient, such as an oil and/or shortening and/or spread and/or other fatty ingredient in beverages, sauces, dairy-based foods (such as milk, yogurt, cheese and ice-cream) and baked goods; or alternately used as a nutritional product, e.g., as a nutritional supplement (in capsule or tablet forms); feed or feed supplement for any animal whose meat or products are consumed by humans; feed or feed supplement for any companion animal, including without limitation dogs, cats, and horses; food supplement, including baby food and infant formula. The term "animal" means any organism belonging to the kingdom Animalia and includes, without limitation, any animal from which poultry meat, seafood, beef, pork or lamb is derived. Seafood is derived from, without limitation, fish, shrimp and shellfish. The term "products" includes any product other than meat derived from such animals, including, without limitation, eggs, milk or other products. When fed to such animals, nutrients such as LC-PUFAs can be incorporated into the flesh, milk, eggs or other products of such animals to increase their content of these nutrients. In addition, when fed to such animals, nutrients such as LC-PUFAs can improve the overall health of the animal.

The compositions of the present invention can be added to a wide range of products such as baked goods, vitamin supplements, diet supplements, powdered drinks, etc. at various stages of production. Numerous finished or semi-finished powdered food products can be produced using the compositions of the present invention.

A partial list of food products comprising the products of the present invention includes doughs, batters, baked food items including, for example, such items as cakes, cheesecakes, pies, cupcakes, cookies, bars, breads, rolls, biscuits, muffins, pastries, scones, and croutons; liquid food products, for example, beverages, energy drinks, infant formula, liquid meals, fruit juices, multivitamin syrups, meal replacers, medicinal foods, and syrups; semi-solid food products such as baby food, yogurt, cheese, cereal, pancake mixes; food bars including energy bars; processed meats; ice creams; frozen desserts; frozen yogurts; waffle mixes; salad dressings; and replacement egg mixes. Also included are baked goods such as cookies, crackers, sweet goods, snack cakes, pies, granola/snack bars, and toaster pastries; salted snacks such as potato chips, corn chips, tortilla chips, extruded snacks, popcorn, pretzels, potato crisps, and nuts; specialty snacks such as dips, dried fruit snacks, meat snacks, pork rinds, health food bars and rice/corn cakes; and confectionary snacks such as candy.

Another product embodiment of the present invention is a medical food. A medical food includes a food which is in a formulation to be consumed or administered externally under the supervision of a physician and which is intended for the specific dietary management of a disease or condition for which distinctive nutritional requirements, based on recognized scientific principles, are established by medical evaluation.

The present invention, while disclosed in terms of specific methods, products, and organisms, is intended to include all such methods, products, and organisms obtainable and useful according to the teachings disclosed herein, including all such substitutions, modifications, and optimizations as would be available to those of ordinary skill in the art. The following examples and test results are provided for the purposes of illustration and are not intended to limit the scope of the invention.

EXAMPLES

Example 1

Preparation of a High Quality Crude Oil

DHA oil-rich *Schizochytrium* microorganisms were grown in a fermentor to produce a fermentation broth. The fermentation broth was harvested and contacted with Alcalase®2.4, a protease that lysed the *Schizochytrium* cells. The resulting lysed cell mixture was an emulsion and was contacted with a 27% solution of isopropanol in water. This mixture was mixed by agitation and then subjected to centrifugation to produce a substantially non-emulsified product having two phases. The heavy phase contained components of the spent fermentation broth, and the light phase contained DHA-rich oil with some isopropanol and water. The light phase was dried to produce a high quality crude oil.

Example 2

Minimal Processing of Algal Oil

This example illustrates the production of minimally processed oils according to the present invention.

Minimally processed oils were produced in large scale. Two hundred kg of high quality crude oil (produced as described in Example 1) produced by a *Schizochytrium* microorganism containing DHA was heated to 65° C. to 70° C. under nitrogen. About 0.2% (w/w of oil) of a 50% citric acid solution was then added into the oil and mixed for 30 to 45 minutes under nitrogen. Subsequently, 0.2 to 0.5% (w/w of oil) filter aid was added into the oil and filtered in order to remove any impurities present in oil. The oil was then deodorized at 210° C. with a feed rate of 180 kg per hour. Deodorized oil was then supplemented with tocopherols, ascorbyl palmitate and rosemary extract. Characteristics of oils at each process step are given in Table 1. The term "PV" means peroxide value; the term "FFA" means free fatty acid; and "p-AV" means p-anisidine value. Recovery from this process was greater than 98%.

TABLE 1

| Process Step | PV (meq/kg) | FFA (%) | p-AV | Phosphorus (ppm) | DHA (% w/w) |
|---|---|---|---|---|---|
| Crude | 0.15 | 0.22 | 3.7 | 3.32 | 34.0 |
| Citric acid-treated | 0.26 | 0.21 | 3.6 | below detection | Not analyzed |
| Deodorized without antioxidants | 0.28 | 0.13 | 4.9 | below detection | Not analyzed |
| Deodorized with antioxidants | 0.0 | 0.15 | 4.0 | below detection | 33.2 |

Example 3a

Physical Refining

This example illustrates the production of minimally processed oils according to the present invention.

Approximately 600 kg of high quality crude oil (produced as described in Example 1) (FFA <0.3%, Phosphorus <10 ppm, PV <2 meq/kg) was taken and heated to 50-55° C. under nitrogen and/or vacuum. About 0.2% (w/w) of 50% citric acid was added and the oil was held at 50-55° C. under nitrogen and/or vacuum for 15 minutes. Trisyl 600 (0.1%-3% w/w, usually 0.25%) was added and the temperature was held between 50-55° C. under nitrogen and/or vacuum for 15 minutes. Tonsil Supreme FF bleaching clay (0.1%-4% w/w, usually less than 0.5%) was added and the oil was heated to 90-95° C. and held under vacuum (>24" Hg) for 30 minutes. Celite (0.1-0.5% w/w, usually 0.2%) was then added and the oil was filtered through a Sparkler filter. The oil was then deodorized at 210-225° C. and a flowrate of 180-225 kg/hr. After deodorization, antioxidants were added. This process yielded an oil that is a semi-solid at room temperature.

Oil yields from this process ranged from ~92-97%. Quality data for these runs with antioxidants are shown in Table 2

TABLE 2

| Trial No. | Initial FFA (%) | Final FFA (%) | Initial PV (meq/kg) | Final PV (meq/kg) | Initial Phos. (ppm) | Final Phos. (ppm) |
|---|---|---|---|---|---|---|
| Trial #1 | <0.1 | 0.11 | 1.15 | 0 | 9.2 | 1.9 |
| Trial #2 | <0.1 | 0.09 | 0.15 | 0 | 5.6 | 0 |
| Trial #3 | 0.28 | 0.19 | 0.25 | <0.1 | 2.6 | 3.4 |
| Trial #4 | 0.23 | 0.21 | 0.26 | 0 | 3.3 | 0 |

FFAs of deodorized oils were measured before and after antioxidants addition. A significant increase in FFAs (about 2×) was observed after adding antioxidants.

Example 3b

Physical Refining (Clear Oil)

This example illustrates the production of minimally processed liquid oils and related solid fat products according to the present invention.

Approximately 1200 kg of high quality crude oil (produced as described in Example 1) (FFA <0.3%, Phosphorus <12 ppm, PV <2 meq/kg) was taken and heated to 50-55° C. under nitrogen and/or vacuum. About 0.2% (w/w) of 50 wt % citric acid was added and the oil was held at 50-55° C. under nitrogen and/or vacuum for 15 minutes. The oil was then chilled from ~55° C. to ~35° C. under nitrogen and/or vacuum using various hold times (0-12 hrs.) and agitator speeds (4-16 rpm). At this time, celite (0.1-0.5% w/w, usually 0.2%) was added and the oil was filtered through a Sparkler filter. The chill filtration step was repeated with the oil being heated under nitrogen and/or vacuum and chilled from ~50° C. to ~30° C. using various hold times (0-12 hrs.) and agitator speeds (4-16 rpm). Celite (0.1-0.5% w/w, usually 0.2%) was added again and the oil was filtered through a Sparkler filter. Next, Trisyl 600 (0.1%-3% w/w, usually 0.25%) was added and the temperature was held between 50-55° C. under nitrogen and/or vacuum for 15 minutes. Tonsil Supreme FF bleaching clay (0.1%-4% w/w, usually 0.5% or less) was added and the oil was heated to 90-95° C. and held under vacuum (>24" Hg) for 30 minutes. Celite (0.1-0.5% w/w, usually 0.2%) was added and the oil was filtered through a Sparkler filter. The oil was then chilled again under nitrogen and/or vacuum from ~40° C. to ~20° C. using various hold times (0-12 hrs.) and agitator speeds (4-16 rpm). Celite (0.1-0.5% w/w, usually 0.2%) was added and the oil was filtered through a Sparkler filter. The oil was then deodorized at 210-225° C. and a flowrate of 180-225 kg/hr. After deodorization, antioxidants were added. This yields an oil that is clear at room temperature. Oil yields from this process range from ~55-60%. Quality data for these runs with antioxidants are shown in Table 3.

TABLE 3

| Trial No. | Initial FFA (%) | Final FFA (%) | Initial PV (meq/kg) | Final PV (meq/kg) | Initial Phos. (ppm) | Final Phos. (ppm) |
|---|---|---|---|---|---|---|
| Trial #1 | 0.21 | 0.1 | 0.32 | 0.5 | <5 | 2.6 |
| Trial #2 | 0.19 | 0.17 | <0.1 | 0.07 | 11 | 3.1 |
| Trial #3 | 0.12 | 0.17 | 0.53 | 0.07 | 3 | 6.5 |
| Trial #4 | 0.18 | 0.08 | 0.26 | 0 | 3.3 | 0.5 |

The material retained by the filter can be treated, for example by heating and filtering, to separate the solid material from the bleaching clay. Heating the material retained by the filter will melt the solids. The melted solids can then be separated from the clay, by filtering, for example, and then resolidified by cooling. The recovered solid will contain about 20-30% PUFA, most of which is DHA. The clear oil and the solid can be used as a food or food additive, for example.

Example 3c

Physical Refining/Silica Refining

This example illustrates the production of minimally processed oils according to the present invention.

Approximately 100 g of high quality crude oil (produced as described in Example 1) (FFA <0.8%, Phosphorus <10 ppm, PV <2 meq/kg) was taken and heated to 50-55° C. under nitrogen. About 0.2% (w/w) of 50 wt % citric acid was added and the oil was held at 50-55° C. under nitrogen and/or vacuum for 15 minutes. Subsequently, 0.5%-1.25% w/w of silica (Brightsorb F100) was added and the oil was heated to 85° C. under vacuum. After 30 minutes holding time, Tonsil Supreme FF bleaching clay (0.5% w/w) was added, the oil was heated to 90-95° C. and held under vacuum (>24" Hg) for 30 minutes. Celite (0.1-0.5% w/w, usually 0.2%) was then added and the oil was vacuum filtered using a Buchner funnel after cooling to 60-65° C. Yields for these tests were between 95-96%. Quality results for these tests are shown in Table 4. The final product was a semi-solid oil. This product could also be deodorized and/or bleached and would remain a semi-solid oil.

TABLE 4

| Trial No. | % Silica | Initial FFA (%) | Final FFA (%) | Initial PV (meq/kg) | Final PV (meq/kg) | Initial AV | Final AV |
|---|---|---|---|---|---|---|---|
| Trial #1 | 0.5% | 0.64 | 0.43 | 1.51 | 1.40 | 6.1 | n/a |
| Trial #2 | 0.8% | 0.64 | 0.34 | 1.51 | 1.33 | 6.1 | n/a |
| Trial #3 | 1.2% | 0.64 | 0.17 | 1.51 | 1.33 | 6.1 | 6.3 |

Example 3d

Modified Caustic Refining

This example illustrates the production of minimally processed oils according to the present invention.

Approximately 600 kg of high quality crude oil (produced as described in Example 1) with FFA up to 0.8% (Phosphorus <12 ppm, PV <2 meq/kg) was taken and heated to 50-55° C. under nitrogen and/or vacuum. About 0.2% (w/w) of 50 wt % citric acid was added and the oil is held at 50-55° C. under nitrogen and/or vacuum for 15 minutes. At this time, 0.1%-0.5% w/w of 50% caustic was added to the oil and held at 60-65° C. for 15-30 minutes (this is ~2-10 times less caustic than the standard amount used). The oil was then centrifuged to remove the soaps from the oil. Trisyl 600 (0.1%-3% w/w, usually 0.25%) was added and the temperature was held between 50-55° C. under nitrogen and/or vacuum for 15 minutes. Tonsil Supreme FF bleaching clay (0.1%-4% w/w, usually 0.5% or less) was added and the oil was heated to 90-95° C. and held under vacuum (>24" Hg) for 30 minutes. Celite (0.1-0.5% w/w, usually 0.2%) was added and the oil was filtered through a Sparkler filter. The oil was then deodorized at 210-225° C. and a flowrate of 180-225 kg/hr. After deodorization, antioxidants were added. This process yielded a semi-solid liquid.

Oil yields from this process range from ~81-91%. Quality data for these runs with antioxidants are shown in Table 5.

TABLE 5

| Trial No. | Initial FFA (%) | Final FFA (%) | Initial PV (meq/kg) | Final PV (meq/kg) | Initial Phos. (ppm) | Final Phos. (ppm) |
|---|---|---|---|---|---|---|
| Trial #1 | 0.26 | <0.1 | 1.37 | 0 | 11.6 | 4.0 |
| Trial #2 | 0.54 | <0.1 | 1.84 | 0 | 9.8 | 4.5 |
| Trial #3 | 0.75 | 0.1 | 0.17 | <0.1 | 8.0 | 5.0 |
| Trial #4 | 0.40 | 0.13 | 0 | <0.1 | 7.0 | 0.6 |
| Trial #5 | 0.23 | 0.08 | 0.31 | 0 | 3.3 | 0.9 |

Example 3e

Modified Caustic Refining/No Centrifugation

This example illustrates the production of minimally processed oils according to the present invention.

Approximately 100 g of high quality crude oil (produced as described in Example 1) (FFA <0.3%, Phosphorus <10 ppm, PV <2 meq/kg) was taken and heated to 50-55° C. under nitrogen and/or vacuum. About 0.2% (w/w) of 50 wt % citric acid was added and the oil was held at 50-55° C. under nitrogen and/or vacuum for 15 minutes. At this time, 0.4% w/w of 50% caustic was added to the oil and held at 60-65° C. for 15-30 minutes (this is ~2-10 times less caustic than the standard amount used). Next, Trisyl 600 (1.5% w/w) was added and the temperature was held between 50-55° C. under nitrogen and/or vacuum for 15 minutes. Celite (0.2% w/w) was added to the oil and it was vacuum filtered using a Buchner funnel. Tonsil Supreme FF bleaching clay (1.0% w/w) was added to the filtered oil and it was heated to 90-95° C. and held under vacuum (>24" Hg) for 30 minutes. Celite (0.2% w/w) was added and the oil was vacuum filtered using a Buchner funnel. Quality results for this test are shown in Table 6. The final product was a semi-solid oil. This product could also be deodorized and/or bleached and would remain a semi-solid oil.

TABLE 6

| Trial No. | Initial FFA (%) | Final FFA (%) | Initial PV (meq/kg) | Final PV (meq/kg) | Initial AV | Final AV |
|---|---|---|---|---|---|---|
| Trial #1 | 0.64 | 0.14 | 1.51 | 1.21 | 6.1 | 5.6 |

Example 4

Dry Fractionation of Crude Algal Oil

This example illustrates the dry fractionation of crude algal oil produced by a *Schizochytrium* microorganism containing DHA into olein and stearin fractions according to the present invention.

Three hundred and fifty kg of the crude oil was subjected to the dry fractionation process according to the invention in order to produce liquid olein and solid stearin fractions. Melting of all crystalline phases within the crude algal oil was ensured by heating the same to 60-70° C. in a vessel with stirring. The material was then cooled rapidly to 20-30° C. during the pre-cooling phase, with the speed of the stirrer increased to 40 revolutions per minute. In order to obtain the highest possible heat transfer coefficient in this phase, a liquid coolant was employed and was water in this example. The temperature of the coolant was not permitted to fall significantly below the nucleation temperature.

The subsequent nucleation phase was conducted within the stirring vessel and was initiated by a reduction of the stirrer speed to 20 revolutions per minute. Further cooling of the oil was done by regulating the temperature difference existing between the coolant and the oil, from the initial oil temperature of 20-30° C., down to the crystallization temperature of about 12-14° C. Once the crystallization temperature has been reached, the stirrer speed was reduced to 15 revolutions per minute. Termination of the crystallization was accomplished by transferring the suspension into a filtration unit immediately after the desired cloud point was reached for the remaining oil, the so-called olein fraction that was still present between the crystals. To monitor the cloud point of the olein fraction, test filtrations of suspension samples were performed during the crystallization phase.

After the crystal suspension has been transferred to the filtration unit, the liquid phase was pressed out through a filter cloth. The filter chamber was charged with a slowly increasing compression pressure that was generated by a mechanical reduction of the volume of the filter chamber, and was slowly increased. The final filtration pressure reached 10 bar. After filtration, the separated fractions were weighed. The olein yield is the weight of the filtrate. The stearin yield is the weight of the crystal mass remaining on the filter. The yields of the measured olein and stearin fractions are given in Table 7. The compositions of the feed materials, olein and stearin fractions are given in Table 8.

TABLE 7

| Parameter | Results |
|---|---|
| Cooling curve (h) | 13 |
| Final Temperature of the Slurry (C.) | 14.2 |
| Solid Fat Content of the Slurry (%) | 7.3 |
| Solid Fat Content of the Stearin (%) | 39.6 |
| Olein Yield (%) | 83.4 |
| Stearin Yield (%) | 14.4 |

TABLE 8

| Parameter | Feed | Olein | Stearin |
|---|---|---|---|
| Moisture content (ppm) | 564-660 | — | — |
| Cloud point (° C.) | 11.5-17.4 | −4.8 to −5.5 | — |
| Iodine value | 235.8-265 | 2604-278.7 | 184.2-210.8 |
| Fatty acid composition (% w/w): | | | |
| 12:0 | 0.2-0.4 | 0.3-0.4 | 0.3-0.6 |
| 14:0 | 10.0-12.6 | 8.6-8.8 | 14.9-16.1 |
| 14:1 | 0.4-0.5 | 0.0-0.4 | 0.5-0.6 |
| 16:0 | 25.3-27.1 | 22.5-23.1 | 36.1-39.1 |
| 16:1 | 0.7-0.8 | 0.0 | 0.0 |
| 18:1n-9 | 0.3-1.9 | 0.3-0.5 | 0.0-0.4 |
| 22:1 | 0.9-1.0 | 1.0-1.1 | 0.7-0.8 |
| 20:5n-3 | 1.4-1.6 | 1.7-1.8 | 1.0-1.5 |
| 22:5n-6 | 14.6-17.1 | 18.0-18.3 | 11.9-12.9 |
| 22:6n-3 | 39.8-43.4 | 45.8-46.0 | 29.1-31.8 |
| Solid fat content (%): | | | |
| 0° C. | 8.7 | 0.0 | 36.3-44.1 |
| 10° C. | 7.5 | — | 34.8-41.2 |
| 15° C. | 6.8 | — | 33.2-38.5 |
| 20° C. | 6.1 | — | 30.5-35.9 |
| 25° C. | 5.4 | — | 28.9-34.0 |
| 30° C. | 3.1 | — | 26.3-31.1 |
| 35° C. | 2.4 | — | 21.0-25.4 |
| 40° C. | 0.8 | — | 12.9-17.2 |
| 45° C. | 0.0 | — | 4.5-5.2 |

TABLE 8-continued

| Parameter | Feed | Olein | Stearin |
|---|---|---|---|
| 50° C. | 0.0 | — | 1.5-2.0 |
| 55° C. | 0.0 | — | 0.0 |

The olein (liquid) and stearin (solid or semi-solid) fractions could be further processed to produced deodorized oil by any of the minimal processing methods described herein and illustrated in the above examples or by any method known in the prior art.

Example 5

The following Example shows a bench-scale process for forming a solid fat product of the invention.

An unwinterized oil extracted by hexane from biomass of a *Schizochytrium* microorganism was heated to 40° C. until all solid material had melted and a homogeneous liquid was formed. In a separate container, monoglyceride and diglyceride emulsifiers (DIMODAN PTK A, available from DANISCO) were melted at the same temperature (40° C.) until completely liquid. The melted emulsifiers were then added to the melted oil and mixed together. The oil/emulsifier mixture was then transferred to an ice bath and mixed constantly while cooling. The cooled product was solid with the consistency of shortening. The product was then transferred to containers and stored.

Example 6

The following Example shows a bench-scale process for fowling a solid fat product with the introduction of nitrogen during the step of solidifying the product.

The procedure was the same as discussed above in Example 5, except that nitrogen was bubbled at a rate of between about 10 and about 50 ml/min into the composition as it cooled, providing extra stability to the product and changing the color/physical characteristics of the product from a dull appearance to a shiny yellow appearance. The cooled product was solid with the consistency of shortening. After cooling, the product was transferred to containers and stored.

Example 7

The following Example shows a pilot or large-scale process for forming a solid fat product.

An unwinterized oil extracted by hexane from biomass of a *Schizochytrium* microorganism was heated to 40° C. until all solid material melted and a homogeneous liquid was formed. In a separate container, the emulsifiers as in Example 5 were melted at the same temperature (40° C.) until completely liquid. The melted emulsifiers were then added to the melted oil (HM) and mixed together. The hot liquid emulsion was introduced to a beaker in ice with stirring to emulate a scrape surface heat exchanger to cool. The composition was cooled from about 40° C. to about 0° C. in about four minutes. During this process nitrogen was introduced into the composition at a rate of between about 10 and about 50 ml/min. After cooling, the resulting crystallized fat was then transferred to containers and stored.

Example 8

The following Example shows a pilot or large-scale process for forming a solid fat product with oil and nutrients added.

The mixture of emulsifier and oil was prepared as described in Example 7. As the mixture cools, it was constantly mixed and water was added at 5% by weight resulting in a product with a slightly different consistency. Ascorbic acid as a free acid was then added to the mixture at about 5% by weight. Folic acid was then added to the mixture at about 0.0008% by weight. The resulting crystallized fat then transferred to containers and stored.

Example 9

The following Example shows the increase in oxidative stability for compositions of the present invention containing ascorbic acid and containing ascorbic acid and folic acid.

Figure 3:
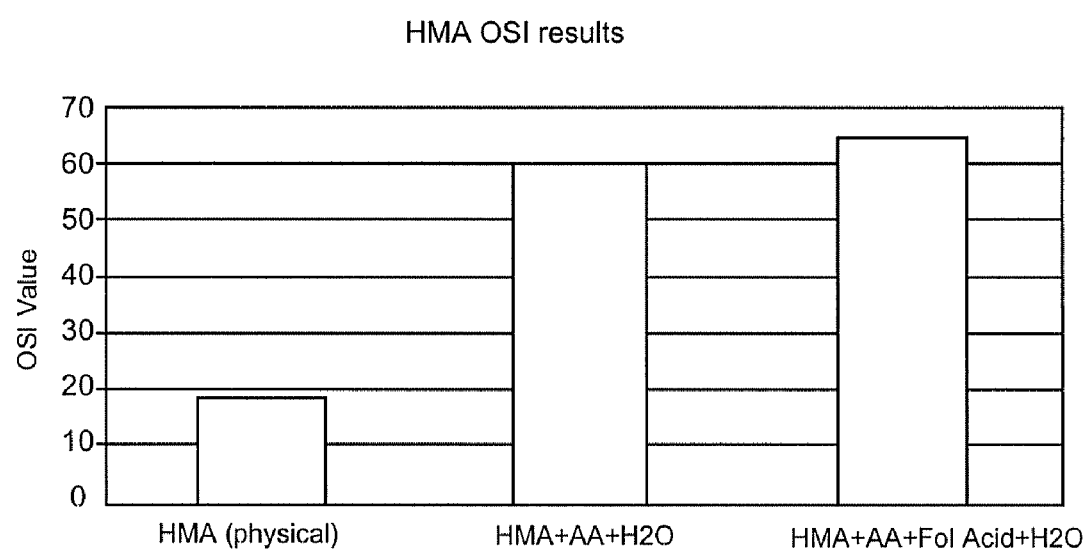
FIG. 3 illustrates a comparison of the oxidative stability index of a solid fat composition, solid fat composition with added ascorbic acid, and a solid fat composition with added ascorbic acid and folic acid.

A solid fat composition of the invention was prepared in accordance with Example 5. Solid fat compositions additionally containing ascorbic acid (5 wt. %) and water (5 wt. %) and containing ascorbic acid (5 wt. %), folic acid (0.0008 wt. %) and water (5 wt. %) were prepared in accordance with Example 1 by the introduction of the additional ingredients during the cooling step. The resulting compositions were evaluated for oxidative stability and the results are shown in FIG. 3. As can be seen, the addition of ascorbic acid and water more than tripled the OSI value of the base composition. Further, the addition of folic acid to the composition with ascorbic acid and water increased the oxidative stability of the composition.

Example 10

Blended Compositions Containing Minimally Processed Oils

The DHA-rich oil from Example 3a and 3d above were blended with ARASCO® (Martek Biosciences, Columbia, Md.) in a ratio of 2:1 to produce ARA- and DHA-containing oil blends.

| Quality Characteristics of blended composition made from minimally processed DHA and ARASCO ® | | |
|---|---|---|
| Parameter | ARASCO ®/ DHA oil (Ex. 2a), 2:1 | ARASCO ® DHA oil (Ex. 2d), 2:1 |
| Physical Description: | | |
| Color (Visual) | Light Yellow | Orange |
| Color (Lovibond) | 1.9 R/70.0 Y | 3.2 R/70.0 Y |
| Oil Clarity at 25° C. | Viscous opaque liquid | Viscous opaque liquid |
| Oil Clarity at 40° C. | Clear liquid | Clear liquid |
| Chemical Analyses: | | |
| DHA (mg/g) | 123 | 127 |
| DHA (area %) | 12.9 | 13.3 |
| ARA (mg/g) | 247.3 | 255.6 |
| ARA (area %) | 27.3 | 28.1 |
| PV (meq/kg) | 0.45 | 0.45 |
| p-AV | 5.9 | 7.2 |
| FFA (%) | 0.07 | 0.07 |
| Moisture & Volatiles (%) | Below detection | Below detection |
| Nonsaponifiables (%) | 1.9 | 1.9 |
| Trans Fatty Acids (%) | Below detection | Below detection |
| Elemental Analyses: | | |
| As | Below detection | Below detection |
| Cu | Below detection | Below detection |
| Fe | Below detection | Below detection |

-continued

Quality Characteristics of blended composition made from minimally processed DHA and ARASCO ®

| Parameter | ARASCO ®/ DHA oil (Ex. 2a), 2:1 | ARASCO ® DHA oil (Ex. 2d), 2:1 |
|---|---|---|
| Pb | Below detection | Below detection |
| Hg | Below detection | Below detection |
| Fatty Acid Profile (Major Fatty Acids): | | |
| 14:0 | 5.2 | 4.0 |
| 16:0 | 17.4 | 16.7 |
| 18:0 | 5.7 | 5.8 |
| 18:1n-9 | 10.9 | 10.9 |
| 18:2n-6 | 4.6 | 4.8 |
| 18:3n-6 | 1.9 | 2.0 |
| 22:0 | 1.0 | 1.0 |
| 20:3n-6 | 2.3 | 2.3 |
| 20:4n-6 | 27.3 | 28.1 |
| 24:0 | 1.1 | 1.1 |
| 22:5n-6 | 4.8 | 5.0 |
| 22:6n-3 | 12.9 | 13.3 |

Example 11

The following example shows a bench-scale process for forming a solid fat product with oil from *Schizochytrium* and palm stearin. An unwinterized fully refined oil produced from biomass of a *Schizochytrium* microorganism was heated to 40-50° C. under nitrogen until all solid material melted and a homogeneous liquid was formed. In a separate container, palm stearin (available from Ciranda Inc., Hudson, Wis.) was melted at the same temperature (40-50° C.) until completely liquid. The ratio of unwinterized oil to palm stearin used was 75 to 25 (%, w/w). Subsequently, melted palm stearin was mixed with unwinterized oil from *Schizochytrium*. In another container, monoglyceride and diglyceride emulsifiers (either Dimodan 930-KA or Grindsted PS 219/B K-A, available from Danisco, Denmark) were heated to 70-75° C. until a homogeneous liquid was formed. The melted oil blend (unwinterized oil and palm stearin) was then added to the melted emulsifier and mixed together. The hot liquid formulation was cooled down to 15° C. in a chiller batch under nitrogen and with agitation. Once the crystallization temperature was reached, the formulation was held for 1 hour at 15° C. with agitation. The resulting crystallized fat formulation was then transferred to containers and stored. The results are shown below in Table 9.

TABLE 9

| Physical and Chemical Properties | Results |
|---|---|
| Peroxide value (meq/kg) | 4.1-8.6 |
| Free fatty acids (%) | 0.15-0.17 |
| p-Anisidine value | Below detection |
| Rancimat (hr) | 10.9-13.5 |
| DHA content (mg/g) | 215.4-239.2 |
| Solid Fat Content (%): | |
| 10.0° C. | 24.4-26.9 |
| 21.1° C. | 18.3-19.8 |
| 26.7° C. | 14.6-16.6 |
| 33.3° C. | 9.2-10.6 |
| 37.8° C. | 7.8-8.1 |

Example 12

The following example shows a bench-scale process for forming a solid fat product with oil from *Schizochytrium* and palm kernel stearin.

An inwinterized fully refined oil produced from biomass of a *Schizochytrium* microorganism was heated to 40-50° C. under nitrogen until all solid material melted and a homogeneous liquid was formed. In a separate container, palm kernel stearin (available from Ciranda Inc., Hudson, Wis.) was melted at the same temperature (40-50° C.) until completely liquid. The ratios of unwinterized oil to palm kernel stearin were ranged from 75:25 to 80:20 (%, w/w). Subsequently, melted palm kernel stearin was mixed with unwinterized oil from *Schizochytrium*. In another container, monoglyceride and diglyceride emulsifiers (either Dimodan 930-KA or Grindsted PS 219/B K-A, available from Danisco, Denmark) were heated to 70-75° C. until a homogeneous liquid was formed. The melted oil blend (unwinterized oil and palm kernel stearin) was then added to the melted emulsifier and mixed together. The hot liquid formulation was cooled down to 15° C. in a chiller batch under nitrogen and with agitation. Once the crystallization temperature has been reached, the formulation was held for 1 hour at 15° C. with agitation. The resulting crystallized fat formulation was then transferred to containers and stored. The results are shown below in Table 10.

TABLE 10

| Physical and Chemical Properties | Results |
|---|---|
| Peroxide value (meq/kg) | 1.1 |
| Free fatty acids (%) | 0.11 |
| p-Anisidine value | Below detection |
| Rancimat (hr) | 7.3 |
| DHA content (mg/g) | 225.8 |
| Solid Fat Content (%): | |
| 10.0° C. | 32.6 |
| 21.1° C. | 18.3 |
| 26.7° C. | 11.2 |
| 33.3° C. | 4.1 |
| 37.8° C. | 2.0 |

Example 13

The following example shows a bench-scale process for forming a solid fat product containing *Schizochytrium* oil and palm kernel stearin with antioxidants added.

An inwinterized fully refined oil produced from biomass of a *Schizochytrium* microorganism was mixed with 0.2% (w/w) antioxidants (containing 10% tocopherol and 10% ascorbyl palmitate) and heated to 40-50° C. under nitrogen until all solid material melted and a homogeneous liquid was formed. In a separate container, palm kernel stearin (available from Ciranda Inc., Hudson, Wis.) was melted at the same temperature (40-50° C.) until completely liquid. The ratio of unwinterized oil to palm kernel stearin was used at 75:25 (%, w/w). Subsequently, melted palm kernel stearin was mixed with unwinterized oil from *Schizochytrium*. In another container, monoglyceride and diglyceride emulsifiers (either Dimodan 930-KA or Grindsted PS 219/B K-A, available from Danisco, Denmark) were heated to 70-75° C. until a homogeneous liquid was formed. The melted oil blend (unwinterized oil and palm kernel stearin) was then added to the melted emulsifier and mixed together. The hot liquid formulation was cooled down to 15° C. in a chiller batch under nitrogen and with agitation. Once the crystallization temperature has been reached, the formulation was held for 1 hour at 15° C. with agitation. The resulting crystallized fat formulation was then transferred to containers and stored. The results are shown below in Table 11.

TABLE 11

| Physical and Chemical Properties | Results |
| --- | --- |
| Peroxide value (meq/kg) | 0.3-0.5 |
| Free fatty acids (%) | 0.15-0.20 |
| p-Anisidine value | Below detection |
| Rancimat (hr) | 18.9-25.0 |
| DHA content (mg/g) | 232-243 |
| Solid Fat Content (%): | |
| 10.0° C. | 30.6-35.6 |
| 21.1° C. | 16.6-21.9 |
| 26.7° C. | 9.7-15.2 |
| 33.3° C. | 2.3-4.2 |
| 37.8° C. | 1.5-3.2 |

Example 14

The following example shows a bench-scale process for forming a solid fat product with *Schizochytrium* oil and palm kernel stearin containing 10-20% (w/w) DHA.

An inwinterized fully refined oil produced from biomass of a *Schizochytrium* microorganism was mixed with 0.2% (w/w) antioxidants (containing 10% tocopherol and 10% ascorbyl palmitate) and heated to 40-50° C. under nitrogen until all solid material melted and a homogeneous liquid was formed. In a separate container, palm kernel stearin (available from Ciranda Inc., Hudson, Wis.) was melted at the same temperature (40-50° C.) until completely liquid. The ratio of unwinterized oil to palm kernel stearin was used at 60:40 (%, w/w). Subsequently, melted palm kernel stearin was mixed with unwinterized oil from *Schizochytrium*. In another container, monoglyceride and diglyceride emulsifiers (either Dimodan 930-KA or Grindsted PS 219/B K-A, available from Danisco, Denmark) were heated to 70-75° C. until a homogeneous liquid was formed. The melted oil blend (unwinterized oil and palm kernel stearin) was then added to the melted emulsifier and mixed together. The hot liquid formulation was cooled down to 15° C. in a chiller batch under nitrogen and with agitation. Once the crystallization temperature has been reached, the formulation was held for 1 hour at 15° C. with agitation. The resulting crystallized fat formulation was then transferred to containers and stored. The results are shown below in Table 12.

TABLE 12

| Physical and Chemical Properties | Results |
| --- | --- |
| Peroxide value (meq/kg) | 0.5-0.7 |
| Free fatty acids (%) | 0.23-0.25 |
| p-Anisidine value | Below detection |
| Rancimat (hr) | 20-26 |
| DHA content (mg/g) | 192-199 |
| Solid Fat Content (%): | |
| 10.0° C. | 39.8-42.6 |
| 21.1° C. | 25.0-27.1 |
| 26.7° C. | 13.6-12.2 |
| 33.3° C. | 2.8-2.9 |
| 37.8° C. | 2.5-3.0 |

Example 15

The following example shows a bench-scale process for forming a solid fat product with *Schizochytrium* oil and palm kernel stearin containing 20-30% (w/w) DHA.

An unwinterized fully refined oil produced from biomass of a *Schizochytrium* microorganism was mixed with 0.2% (w/w) antioxidants (consist of 10% tocopherol and 10% ascorbyl palmitate) and heated to 40-50° C. under nitrogen until all solid material melted and a homogeneous liquid was formed. In a separate container, palm kernel stearin (available from Ciranda Inc., Hudson, Wis.) was melted at the same temperature (40-50° C.) until completely liquid. The ratios of unwinterized oil to palm kernel stearin were ranged from 75:25 to 85:15 (%, w/w). Subsequently, melted palm kernel stearin was mixed with unwinterized oil from *Schizochytrium*. In another container, monoglyceride and diglyceride emulsifiers (either Dimodan 930-KA or Grindsted PS 219/B K-A, available from Danisco, Denmark) were heated to 70-75° C. until a homogeneous liquid was formed. The melted oil blend (unwinterized oil and palm kernel stearin) was then added to the melted emulsifier and mixed together. The hot liquid formulation was cooled down to 15° C. in a chiller batch under nitrogen and with agitation. Once the crystallization temperature has been reached, the formulation was held for 1 hour at 15° C. with agitation. The resulting crystallized fat formulation was then transferred to containers and stored. The results are shown below in Table 13.

TABLE 13

| Physical and Chemical Properties | Results |
| --- | --- |
| Peroxide value (meq/kg) | 0.0-0.6 |
| Free fatty acids (%) | 0.16-0.24 |
| p-Anisidine value | 0.0-5.0 |
| Rancimat (hr) | 19.6-22.4 |
| DHA content (mg/g) | 236-283 |
| Solid Fat Content (%): | |
| 10.0° C. | 27.7-32.1 |
| 21.1° C. | 15.2-18.1 |
| 26.7° C. | 9.8-11.6 |
| 33.3° C. | 4.5-4.9 |
| 37.8° C. | 2.7-2.9 |

Example 16

The following example shows a bench-scale process for forming a solid fat product containing *Schizochytrium* oil and palm kernel stearin with >30% (w/w) DHA.

An unwinterized fully refined oil produced from biomass of a *Schizochytrium* microorganism was mixed with 0.2% (w/w) antioxidants (10% tocopherol and 10% ascorbyl palmitate) and heated to 40-50° C. under nitrogen until all solid material melted and a homogeneous liquid was formed. In a separate container, palm kernel stearin (available from Ciranda Inc., Hudson, Wis.) was melted at the same temperature (40-50° C.) until completely liquid. The ratio of unwinterized oil to palm kernel stearin used was 80:20 (%, w/w). Subsequently, melted palm kernel stearin was mixed with unwinterized oil from *Schizochytrium*. In another container, monoglyceride and diglyceride emulsifiers (either Dimodan 930-KA or Grindsted PS 219/B K-A, available from Danisco, Denmark) were heated to 70-75° C. until a homogeneous liquid was formed. The melted oil blend (unwinterized oil and palm kernel stearin) was then added to the melted emulsifier and mixed together. The hot liquid formulation was cooled down to 15° C. in a chiller batch under nitrogen and with agitation. Once the crystallization temperature has been reached, the formulation was held for 1 hour at 15° C. with agitation. The resulting crystallized fat formulation was then transferred to containers and stored. The results are shown below in Table 14.

TABLE 14

| Physical and Chemical Properties | Results |
| --- | --- |
| Peroxide value (meq/kg) | 0.2-0.4 |
| Free fatty acids (%) | 0.12-0.17 |
| p-Anisidine value | Below detection |
| Rancimat (hr) | 18.9-19.9 |
| DHA content (mg/g) | 310-319 |
| Solid Fat Content (%): | |
| 10.0° C. | 23.1-28.5 |
| 21.1° C. | 11.4-16.5 |
| 26.7° C. | 6.3-10.7 |
| 33.3° C. | 4.3-5.0 |
| 37.8° C. | 2.9-3.1 |

Example 17

The following example shows a bench-scale process for forming a solid fat product containing *Schizochytrium* oil and palm kernel stearin with Natural Butter Flavor and Bitterness Masker added.

An unwinterized fully refined oil produced from biomass of a *Schizochytrium* microorganism was mixed with 0.2% (w/w) antioxidants (10% tocopherol and 10% ascorbyl palmitate), 0.1-0.15% (w/w) natural butter flavor (available from Danisco) and 0.03-0.05% (w/w) natural bitterness masker (available from Firmenich Inc.). It was then heated to 40-50° C. under nitrogen until all solid material melted and a homogeneous liquid was formed. In a separate container, palm kernel stearin (available from Ciranda Inc., Hudson, Wis.) was melted at the same temperature (40-50° C.) until completely liquid. The ratio of unwinterized oil to palm kernel stearin used was 80:20 (%, w/w). Subsequently, melted palm kernel stearin was mixed with unwinterized oil from *Schizochytrium*. In another container, monoglyceride and diglyceride emulsifiers (Dimodan 930-KA, available from Danisco, Denmark) were heated to 70-75° C. until a homogeneous liquid was formed. The melted oil blend (unwinterized oil and palm kernel stearin) was then added to the melted emulsifier and mixed together. The hot liquid formulation was cooled down to 15° C. in a chiller batch under nitrogen and with agitation. Once the crystallization temperature has been reached, the formulation was held for 1 hour at 15° C. with agitation. The resulting crystallized fat formulation was then transferred to containers and stored. The results are shown below in Table 15.

TABLE 15

| Physical and Chemical Properties | Results |
| --- | --- |
| Peroxide value (meq/kg) | Below detection |
| Free fatty acids (%) | 0.19-0.2 |
| p-Anisidine value | Below detection |
| Rancimat (hr) | 28.3-28.5 |
| DHA content (mg/g) | 230-283 |
| Solid Fat Content (%): | |
| 10.0° C. | 21.8-27.9 |
| 21.1° C. | 14.0-14.8 |

TABLE 15-continued

| Physical and Chemical Properties | Results |
| --- | --- |
| 26.7° C. | 7.2-8.6 |
| 33.3° C. | 2.6-4.0 |
| 37.8° C. | 1.9-2.2 |

The principles, preferred embodiments and modes of operation of the present invention have been described in the foregoing specification. The invention which is intended to be protected herein should not, however, be construed as limited to the particular forms disclosed, as these are to be regarded as illustrative rather than restrictive. Variations and changes may be made by those skilled in the art without departing from the spirit of the present invention. Accordingly, the foregoing best mode of carrying out the invention should be considered exemplary in nature and not as limiting to the scope and spirit of the invention as set forth in the appended claims.

What is claimed is:

1. A method for producing a solid fat composition comprising:
   a) mixing a first oil comprising saturated fat and a second microbial oil comprising at least one long chain polyunsaturated fatty acid (LC-PUFA) with at least one emulsifier to form a mixture; and
   b) solidifying the mixture to form a solid fat composition, wherein the ratio of the second microbial oil to the first oil comprising saturated fat is from 75:25 to 85:15, wherein the second microbial oil comprises between about 5 wt. % and about 70 wt. % LC-PUFA and between about 20 wt. % and about 60 wt. % saturated fat, and wherein the saturated fat is added exogenously.

2. The method of claim 1, wherein the second microbial oil is unwinterized.

3. The method of claim 1, wherein the first oil comprising saturated fat is not hydrogenated.

4. The method of claim 1, wherein the second microbial oil is from a microorganism selected from the group consisting of microorganisms of the genus *Thraustochytrium*, microorganisms of the genus *Schizochytrium*, microorganisms of the genus *Althornia*, microorganisms of the genus *Aplanochytrium*, microorganisms of the genus *Japonochytrium*, microorganisms of the genus *Elina*, microorganisms of the genus *Crypthecodinium*, and mixtures thereof.

5. The method of claim 4, wherein the microorganism is selected from the group consisting of microorganisms of the genus *Thraustochytrium*, microorganisms of the genus *Schizochytrium*, microorganisms of the genus *Crypthecodinium*, and mixtures thereof.

6. The method of claim 1, wherein the second microbial oil comprises an LC-PUFA having a carbon chain length of at least 20.

7. The method of claim 6, wherein the LC-PUFA has at least three double bonds.

8. The method of claim 6, wherein the LC-PUFA comprises docosahexaenoic acid.

9. The method of claim 8, wherein the oil comprises at least about 50 weight percent docosahexaenoic acid.

10. The method of claim 6, wherein the LC-PUFA comprises an LC-PUFA selected from the group consisting of docosapentaenoic acid, arachidonic acid, and eicosapentaenoic acid.

11. The method of claim 1, wherein the solid fat composition has a homogeneous texture.

12. The method of claim 1, wherein the solid fat composition is a shortening.

13. The method of claim 1, wherein the emulsifier is selected from the group consisting of a monoglyceride, a diglyceride, a mono/diglyceride combination, a lecithin, a lactylated mono-diglyceride, a polyglycerol ester, a sucrose fatty acid ester, a sodium steroyl lactylate, a calcium steroyl lactylate, and combinations thereof.

14. The method of claim 1, wherein the emulsifier is present in an amount of between about 0.01 weight percent and about 2.0 weight percent.

15. The method of claim 1, wherein the solid fat composition has a melting temperature of at least about 20° C.

16. The method of claim 1, wherein solidifying the mixture controls formation of crystals in the solid fat composition.

17. The method of claim 16, wherein the crystals comprise β-prime crystals.

18. The method of claim 1, wherein the first oil comprising saturated fat and the second microbial oil comprising at least one LC-PUFA is heated.

19. The method of claim 1, wherein the emulsifier is heated.

20. The method of claim 1, wherein the mixing comprises agitating the mixture.

21. The method of claim 1, wherein the solidifying the mixture comprises cooling the mixture.

22. The method of claim 21, wherein the cooling comprises cooling the mixture to a temperature of about 0° C. to about 3° C.

23. The method of claim 21, wherein the solidifying further comprises mixing the mixture during the cooling.

24. The method of claim 21, wherein the mixture is cooled at a rate of between about 1° C./min and about 20° C./min.

25. The method of claim 1, wherein the solidifying comprises introducing nitrogen into the mixture.

26. The method of claim 1, further comprising adding an antioxidant.

27. The method of claim 1, wherein the solid fat composition has an OSI value of at least about 20.

28. The method of claim 1, wherein the solid fat composition is selected from the group consisting of a food product, a nutritional product and a pharmaceutical product.

29. The method of claim 1, further comprising adding the solid fat composition to a product selected from the group consisting of a food product, a nutritional product and a pharmaceutical product.

30. A method for producing a solid fat composition comprising:
   a) mixing a first oil comprising saturated fat and a second microbial oil comprising at least one long chain polyunsaturated fatty acid (LC-PUFA) with at least one emulsifier to form a mixture;
   b) solidifying the mixture to form a solid fat composition; and
   c) adding a water-soluble liquid, wherein the ratio of the second microbial oil to the first oil comprising saturated fat is from 75:25 to 85:15.

* * * * *